US011504261B2

(12) United States Patent
Dellanno

(10) Patent No.: US 11,504,261 B2
(45) Date of Patent: *Nov. 22, 2022

(54) FORWARD HEAD POSTURE CORRECTION COLLAR ASSEMBLY

(71) Applicant: Ronald P. Dellanno, Bloomfield, NJ (US)

(72) Inventor: Ronald P. Dellanno, Bloomfield, NJ (US)

(73) Assignee: Ronald P. Dellanno, Bloomfield, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/596,444

(22) Filed: Oct. 8, 2019

(65) Prior Publication Data
US 2020/0038224 A1 Feb. 6, 2020

Related U.S. Application Data

(63) Continuation-in-part of application No. 16/362,098, filed on Mar. 22, 2019.

(60) Provisional application No. 62/646,523, filed on Mar. 22, 2018.

(51) Int. Cl.
*A61F 5/00* (2006.01)
*A61F 5/055* (2006.01)

(52) U.S. Cl.
CPC .................................. *A61F 5/055* (2013.01)

(58) Field of Classification Search
CPC .. A61F 5/048; A61F 5/05; A61F 5/055; A61F 5/05816; A61F 5/05883; A61F 5/05891; A61F 5/32; A61F 5/34; A61F 5/3707; A61F 2250/0004; A61F 5/30; A61H 1/008; A61H 1/0292; A61H 1/0296; A63B 71/1291
USPC .......... 602/13, 17, 18, 19, 32; 128/857, 869, 128/845
See application file for complete search history.

(56) References Cited

U.S. PATENT DOCUMENTS

| 4,643,174 A | 2/1987 | Horiuchi |
| 5,575,763 A | 11/1996 | Nagata |
| 7,951,102 B2 | 5/2011 | Gefen et al. |

(Continued)

OTHER PUBLICATIONS

Rice University, Rice University Students Create Better Cervical Collar, Apr. 9, 2012, Youtube, https://www.youtube.com/watch?v=J8wnuXQTm-k&feature=emb_logo (Year: 2012).*

*Primary Examiner* — Michelle J Lee
*Assistant Examiner* — Michael Milo
(74) *Attorney, Agent, or Firm* — G. Glennon Troublefield

(57) ABSTRACT

The posture correction collar is able to adjust a forward translation of the head of a hypothetical wearer relative to the shoulders. The collar comprises a first assembly having a support member shaped and dimensioned to wrap around at least a portion of the upper area of the body of the wearer. A second assembly is movable relative to the first assembly. The second assembly has a first adjustable mechanism to progressively and incrementally move relative to the first support assembly and a second adjustable mechanism to engage a portion of the head of the wearer. The first and second adjustable mechanisms are used to correct the posture of the wearer by promoting progressive and incremental movements of the head relative to the shoulders to achieve an anatomically desired condition.

10 Claims, 22 Drawing Sheets

(56) References Cited

U.S. PATENT DOCUMENTS

| | | | |
|---|---|---|---|
| 8,764,693 B1 | 7/2014 | Graham | |
| 2005/0113728 A1* | 5/2005 | Heinz et al. | A61F 5/055 602/18 |
| 2007/0079832 A1 | 4/2007 | Baldauf et al. | |
| 2007/0270728 A1* | 11/2007 | Chao | A61F 5/055 602/18 |
| 2009/0149788 A1* | 6/2009 | Dellanno | A61F 5/055 602/18 |
| 2009/0247918 A1 | 10/2009 | Patron | |
| 2010/0087764 A1* | 4/2010 | Linares | A61F 5/055 602/18 |
| 2010/0298748 A1* | 11/2010 | Rosenfeld | A61F 5/055 602/17 |
| 2015/0245940 A1* | 9/2015 | Hardcastle | A63B 21/4025 602/18 |
| 2015/0328038 A1 | 11/2015 | Rosenfeld et al. | |

* cited by examiner

FORWARD HEAD POSTURE CORRECTION COLLAR ASSEMBLY

CROSS-REFERENCE TO RELATED APPLICATIONS

This is a continuation in part application that claims priority to non-provisional utility application Ser. No. 16/362,098, filed on Mar. 22, 2019, titled "Forward Head Posture Correction Collar Assembly", which claimed priority to provisional application Ser. No. 62/646,523, flied on Mar. 22, 2018, titled "Forward Head Posture Correction Collar", the contents of both being incorporated by reference herein in their entirety.

FIELD OF THE INVENTION

This invention relates generally to orthopedic correction devices and apparatus, and more specifically is directed to a therapeutic head position correction collar assembly.

BACKGROUND OF THE INVENTION

Forward head positioning is an increasingly observed malady in our society. It is well known to orthopedists, chiropractors and other medical practitioners that the human head in its normal position should sit in an anatomically direct fashion on the neck and shoulders. Partly because of certain increasing habits in our society the head can become displaced to a posture where instead of sitting directly on the neck and over the shoulders, it is displaced forward of that normal position to what is called a "forward head posture" position (or "FHP"). FHP is identifiable when the position of the ear is forward when compared to the shoulder, as opposed to being posited directly over it. FHP has become so widespread that it may already constitute a health hazard having the ramifications of a pandemic, since when left untreated FHP can develop degenerative and disabling joint diseases affecting countless numbers of people.

There are numerous reasons why FHP is becoming such a common problem. For example, vastly increased use of computer screens accustoms the operator to move and maintain his or her head (and ears) in the undesirable forward head posture. The problem is exacerbated in children and in young adults by long hours devoted to video games, not to mention conventional television watching. Yet another source believed to be responsible for the malady particularly in children, is the present custom of children carrying extremely heavy backpacks to and from school. The weight of such backpacks is so high as to require head placement in a forward position to balance the load, which results in the increasing observation of forward head posture in both children and young adults. As another example, FHP occurs in athletes playing contact sports, such as football or soccer, in which a given player's head will move involuntarily in an unplanned direction. In football, it is known that a players head will move in several directions when the player is tackled or blocked. In that instance, the head will move in a direction that causes stress on the spine and the head translates forward of the shoulders. The same type of movement may be experienced when a given player is using his or her head during soccer to hit the soccer ball.

Basic damage resulting from forward head posture (FHP) arises because the cervical portion of the spine can become chronically misaligned. The cervical portion of the spine is formed by the first seven vertebrae (numbered C1 to C7) of the spine and is located in the neck. The cervical spine supports the head and enables its flexibility to allow normal head movement. Proper alignment of the cervical spine promotes blood flow to the brain and promotes the function of other organs and systems within the human body. In a normal state, the cervical spine is curved, which is known as cervical lordosis. A lordotic curve in the spine has the opening of the "C" facing posteriorly, that is, towards the back. A normal range of the cervical lordosis ranges from approximately 36° to approximately 44°, but changes when the head translates due to FHP.

The cervical lordosis is part of the normal curvature of the overall spine or vertebrae of the human body which has sections of lordosis and kyphosis. Kyphosis describes the "C" shaped curve in the thoracic spine in which the opening of the "C" is in the front of the human body when viewed from the frontal (coronal) plane. The coronal plane divides the body into a front and a back portion and a sagittal (lateral plane) divides the body into left and right (but not necessarily) equal portions. For purposes of describing the directional function of the changes to lordosis the present invention will concern a human body in a typical anatomical position that has X, Y and Z axes. The Z-axis is oriented in a plane parallel to an imaginary horizontal axial plane that extends intermediate the anterior and posterior portion of the body. The corresponding vertical axis is referred to as the Y-axis and the horizontal left to right side axis is referred to as the X-axis. The Y-axis extends from the top of the head to the bottom of the feet. The X-axis extends from the left side of the body to the right side of the body. The terms right and left as used herein will refer to the individual's right and left side, respectively, when facing the front part of the body, i.e., the anatomical position of the body.

Keeping the anatomical position of the human body in mind, FHP will translate the head forward of the shoulders along the Z-axis. Every inch the head moves forward of the shoulders dramatically adds mechanical weight or loads to the neck. For example, an individual with poor posture may have his or her head translate a number of degrees from the anatomically correct position, which is considered zero degrees. In a normal anatomical position, the head is aligned forward of the shoulders in the zero degree (0°) position, such that the ears are lined up with the center of the shoulder. In that positon, there is about 10-12 lbs. of weight loaded to the neck and cervical spine. When the head moves forward, such that the ears are displaced away from the centerline and no longer are positioned over the shoulders, there is an increase in the number of pounds imposed on the neck. A fifteen degree (15°) displacement can create up to 27 lbs of additional weight and a sixty degree (60°) displacement can impose an additional 60 lbs on the neck. The forward positioning of the head can pull the spine out of its anatomical alignment, and can add up to 30 lbs of abnormal leverage on the cervical spine and, as a result, can pull the cervical spine out of alignment.

FIG. 23 illustrates a side view the progression of FHP which translates the head and the impact on the cervical spine on a hypothetical human body. As shown in FIG. 23, the head translates such that the position of the ears relative to the shoulder move along the Z-axis (from the right side of the paper toward the left side of the paper). As a result of the forward head translation from 0° (approximately 10-12 lbs) to 60° (approximately 60 lbs), the natural lordotic curvature of the cervical spine decreases. Movements in head posture forces the human body to recruit muscles in the upper back and neck areas to work harder to keep the head (including the chin) properly aligned, as opposed to dropping forwards towards the chest area. It is known by those of ordinary skill in the art that FHP may result in the loss of 30% of vital lung capacity due to the loss of the cervical lordosis. When the natural lordotic curvature of the cervical spine changes problems can arise which present in a number of symptoms, such as neck and back pain, neck stiffness, vertigo and nausea, headaches and tinnitus, high blood pressure, insomnia and fatigue, numbness or tingling sensation in the neck, respiratory changes, and other symptoms known in the medical field.

While the difficulties arising from FHP are certainly well recognized in the healing arts, efforts to correct same by treatment with orthopedic devices and the like have not been successful. Most efforts have taken the form of using cervical collars to immobilize the neck. The objective of these collars has simply been to utilize traction to displace the head from its improper position. Neither these prior art collars, nor to the best of applicant's knowledge any other presently available devices and/or apparatus, are however effective in reversing the damaging effects of FHP.

Many of the prior art devices that have been used or proposed, while achieving adjustments along the Z-axis are not otherwise concerned with simultaneously improving cervical lordosis. Most cervical collars are designed to immobilize the neck and/or cause axial translation to decompress the cervical spine while causing the cervical spine straightening. This may produce mixed benefits, as ligament impairment cannot improve around a straightened cervical curve, as this is an abnormal alignment, which will ultimately result in permanent arthritic changes to the cervical joints. Ligament rehabilitation requires improvement of joint alignment over time. Most current extension traction therapy designed to improve cervical lordosis is practiced for 20 minutes or less.

Dellanno, U.S. Pat. No. 8,038,635, the disclosure of which is herein incorporated by reference in its entirely, teaches a forward head position correction collar featuring in combination a shoulder collar assembly, a chin-mastoid piece for engaging and positioning the head of a wearer of the collar and a means interconnecting the chin-mastoid piece to the shoulder collar assembly for manually and incrementally adjusting the chin-mastoid piece with respect to the shoulder collar assembly in an anterior/posterior (Z-axis) direction along the Z-axis.

It is desirable to provide an adjustable therapeutic collar for use in correcting FHP and to restore cervical lordosis. It is desirable to provide a forward head position correction collar featuring in combination a shoulder collar assembly, a chin rest and cheekbone elements for engaging and repositioning the head of a wearer of the collar. It is preferable to engage and position using force applied to the cheek jaw rather than the chin. One objective of the present invention is to improve cervical lordosis with a correction collar that can be advantageously used by an individual or a medical provider over many hours. It is another objective of the invention to provide a therapeutic collar that is easy to use, comfortable to wear by an individual wearer and is adjustable. It is a further objective of the invention to provide a therapeutic collar that is light weight and has can be used at work or at home or even during hours facing a screen to avoid unhealthy postures that impair the health of an injured neck.

SUMMARY OF THE INVENTION

The present invention features a posture correction collar to adjust forward translation of the head of a hypothetical wearer relative to the shoulders, when the body is viewed perpendicularly to a sagittal plane (i.e., from the side of the body). The collar comprises a support structure having a support member that shaped and dimensioned to wrap around and engage at least a portion of the upper area of the body of the wearer when the collar is used. An adjustable structure is movable relative to the support structure. The adjustable structure has a first adjustable mechanism to progressively and incrementally move relative to the first support assembly and a second adjustable mechanism to engage a portion of the head of the wearer. The first and second adjustable mechanisms are used to correct the posture of the wearer, by promoting progressive and incremental movement of the head relative to the shoulders to achieve an anatomically desired condition. In a preferred embodiment, the collar comprises an adjustable lordosis displacement assembly that is secured to the first support assembly. The adjustable displacement assembly has an adjustment assembly to progressively and incrementally apply a corrective force to the rear of the wearer. The corrective force is applied to the upper, middle or lower cervical spine to translate the head and to selectively restore the approximate lordotic curvature of the cervical spine of the wearer to an anatomically desired position. The collar is advantageously used to correct forward head translation and adjusting the posture of the wearer.

BRIEF DESCRIPTION OF DRAWINGS

For the purpose of illustrating the invention, there is shown in the drawings a form which is presently preferred; it being understood, however, that this invention is not limited to the precise arrangements and instrumentalities shown.

DETAILED DESCRIPTION OF THE DRAWINGS

The present invention is directed to a head position correction collar which utilizes mild axial translation of the head and preferably corrective cervical translation forces along a line parallel to a hypothetical sagittal plane. The invention provides an orthopedic correction device which can be readily used by a patient suffering from FHP, which can reverse the damaging effects of compressive loading, shear, and undesired neck movements which FHP generates at all seven cervical vertebra of the patient.

Figure 1:
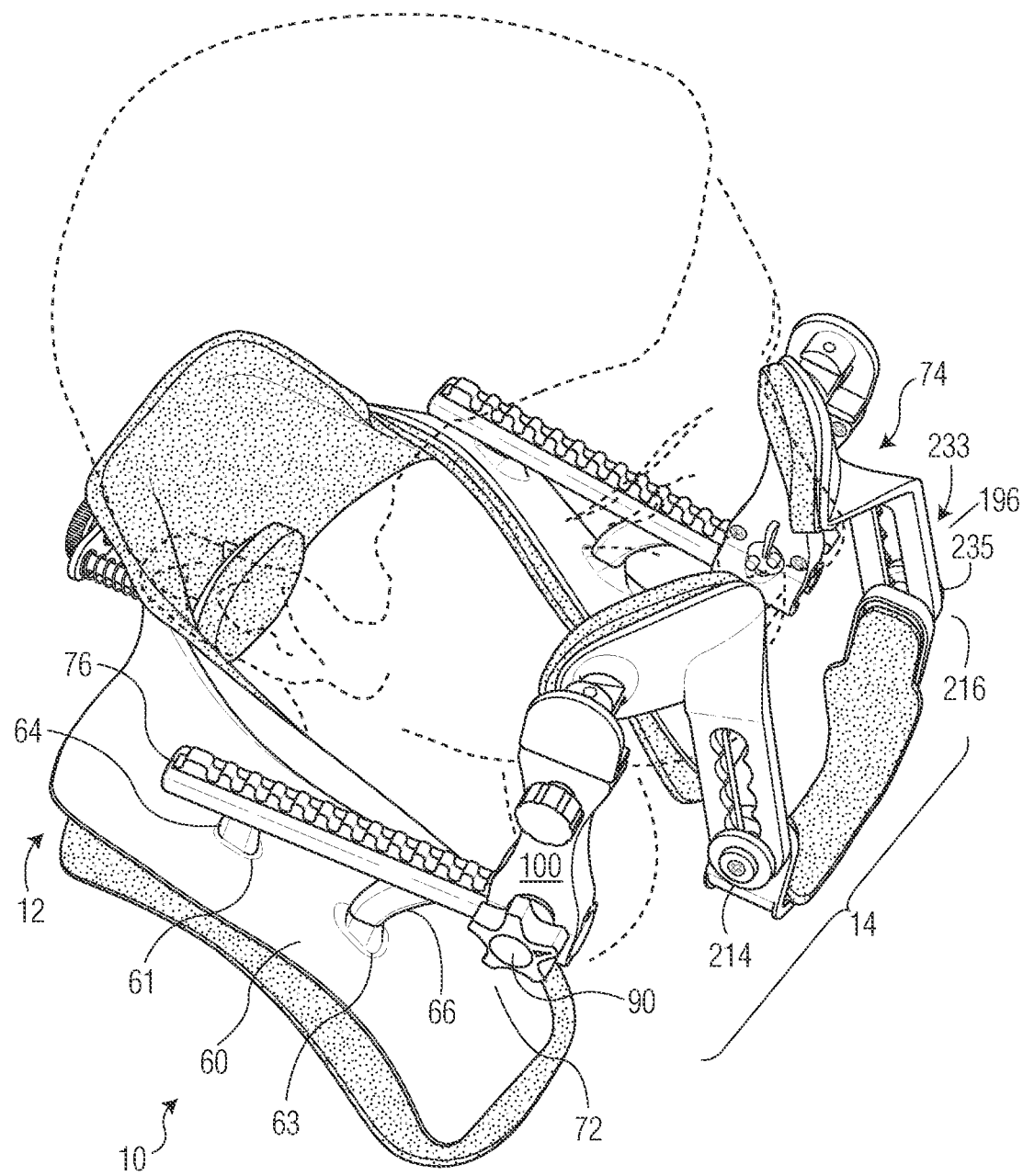
FIG. 1 is a side perspective view of a forward head posture correction collar of the present invention in an assembled condition, mounted to the hypothetical head of a wearer shown in phantom.
Figure 2:
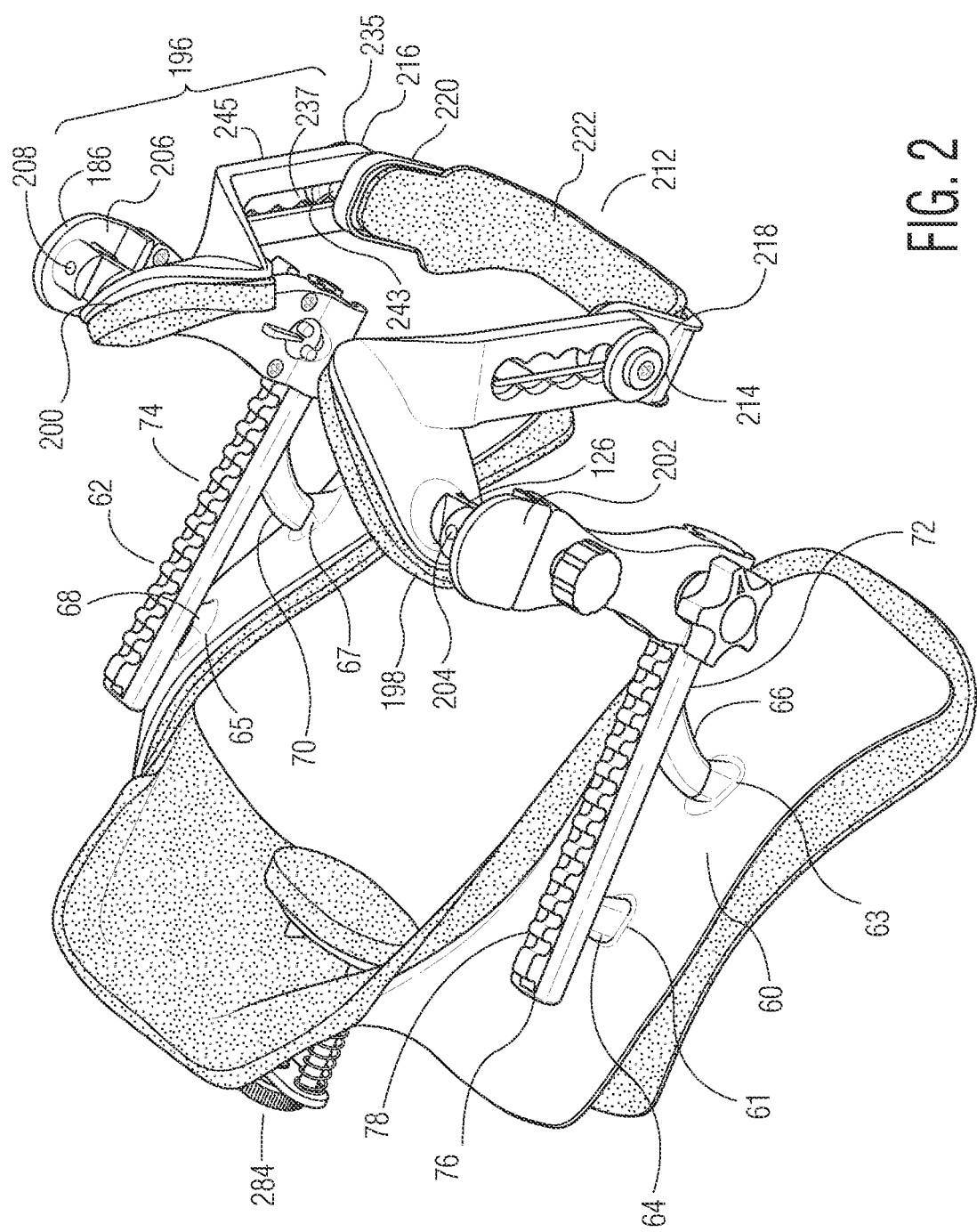
FIG. 2 is a perspective view of the collar shown in FIG. 1 without the head of the wearer, showing a support structure and a adjustable structure which contain components that are bilaterally symmetrical to each other.

In the views of FIGS. 1 and 2, an adjustable head correction collar 10 is shown in a fully assembled, therapeutic condition. The collar 10 comprises a support structure 12 that can be mounted on to a body of a hypothetical wearer, preferably around the shoulders. A second adjustable structure 14 is operatively adapted to move relative to the first support structure 12. The combined use of first support structure 12 and second adjustable structure 14 is advantageously used to reposition the head (shown in phantom in FIG. 1) of the wearer relative to the shoulders, to therapeutically treat patients experiencing FHP or other anatomical or physical maladies. For example, patients experiencing FHP will suffer from their head moving out of its preferred anatomical position (i.e., forward head translation (FHT)), in which the ears of the head are displaced from their ideal axial alignment with the shoulders.

Figure 23:
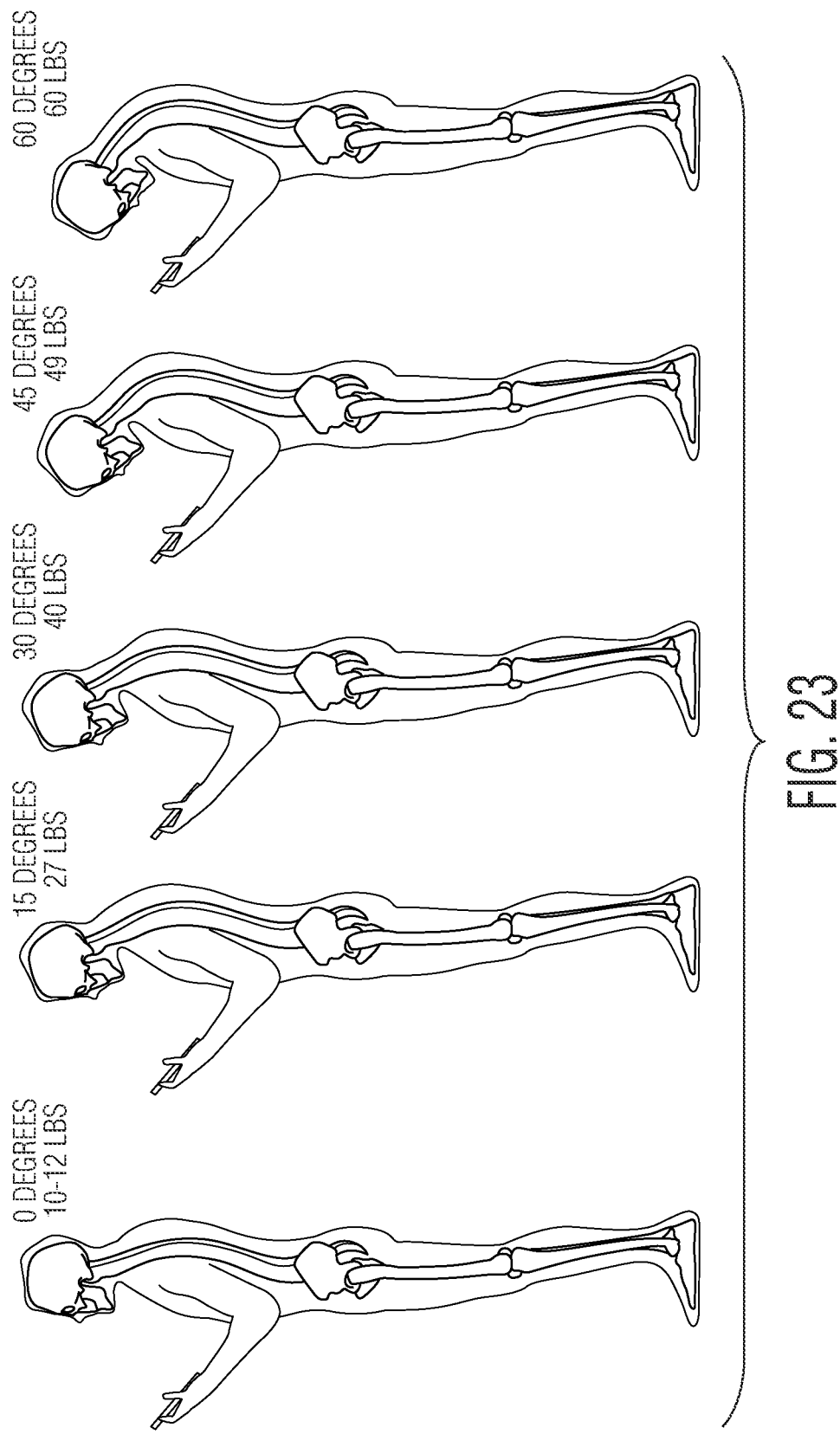
FIG. 23 is a schematic cross-sectional view depicting sequential changes that occur in the wearer's head position and spinal configuration when the head translates relative to the shoulders, which cause forward head posture.

As shown in FIG. 23, in a natural standing position, when looking into the paper there is a hypothetical sagittal plane (not shown). The sagittal plane is an anatomical boundary that exists between the right and left sides of the body, which extends along an imaginary line that is parallel to the longitudinal axis of the body, forming the Y-axis. An imaginary transverse plane extends horizontally from the anterior or posterior portions of the body, which coincides with the Z-axis (which extends intermediate the left and right sides of the paper) Perpendicular to the Z-axis is the X-axis which is in a direction into and out of the paper. The X-axis is aligned with a coronal (frontal) plane, which divides the boding into dorsal and ventral sections. The X-, Y-, and Z-axes, along with the sagittal and coronal planes, provide perspective to understand how the present invention can be used to address posture relative to FHP and other changes to the axial musculoskeletal system, particularly the head and spine.

A normal healthy spine when viewed from the side is made up of three curves, defined by the cervical, thoracic and lumbar vertebrae portions of the spine. According to the American Physical Therapy Association, good standing posture occurs when there is alignment of the ear, shoulder, hip and ankle when the body is viewed from the side. For example, a normal alignment is depicted in the cross-section side view of the hypothetical individual illustrated in FIG. 23 (on the farthest left side of the paper) in which the displacement of the head is at zero degrees (0°). The ears should be level and roughly balanced over the shoulders and the shoulders should be balanced over the pelvis. The spine has a natural elongated S-Shape that provides a spring to cushion the joints, and promotes a healthy nervous system and other functions of the body, including functions directed to the respirator and cardiopulmonary systems. When the spinal alignment is compromised by patients suffering from FHP, there is a loss of curvature or lordosis in the spine, such as in the cervical spine areas which impacts how the systems of the body operate. As depicted in FIG. 23, as the head moves away from its normal position and forward head translation occurs, increased forces or loads are formed which alter the lordotic curve of the cervical spine thereby creating what is called forward head posture. As one illustration, when an individual looks at his or telephone, there is increased extension of the cervical spine which can lead to a variety of problems, such as pain and discomfort. Accordingly, collar 10 of the present invention is used to therapeutically address the increased extension of the cervical spine, return the head close to its normal anatomically desired position, and preferably restore some of the natural curvature of the cervical spine and better spinal alignment. It should be understood by those of ordinary skill that as the body ages, there are certain anatomical changes that may occur in the spine due to trauma, medical conditions, or the natural aging process. The present invention can be adapted for use by medical providers to help the individual patients optimize the alignment of their spine (particularly the cervical spine) that best suits their body to promote their long term health.

Returning to FIGS. 1 and 2, the components of the collar 10 are shown in a fully assembled condition. The collar 10 is made of relatively sturdy, but flexible material using known polymers, such as nylon, polyethylene or polypropylene. Polymeric material is preferred to reduce the weight of collar 10 weight, yet retain components that are flexible to accommodate different individuals who have a variety of anatomic shapes and sizes. Pliable material, such as carbon fibers bonded with resins, graphene, and medical grade plastics may be used in placed of nylon. Nylon increases the operability of collar 10 when it is mounted on and taken off of the individual wearer, thereby avoiding degrading of its function by fatigue that would otherwise occur due to frequent use.

Figure 4:
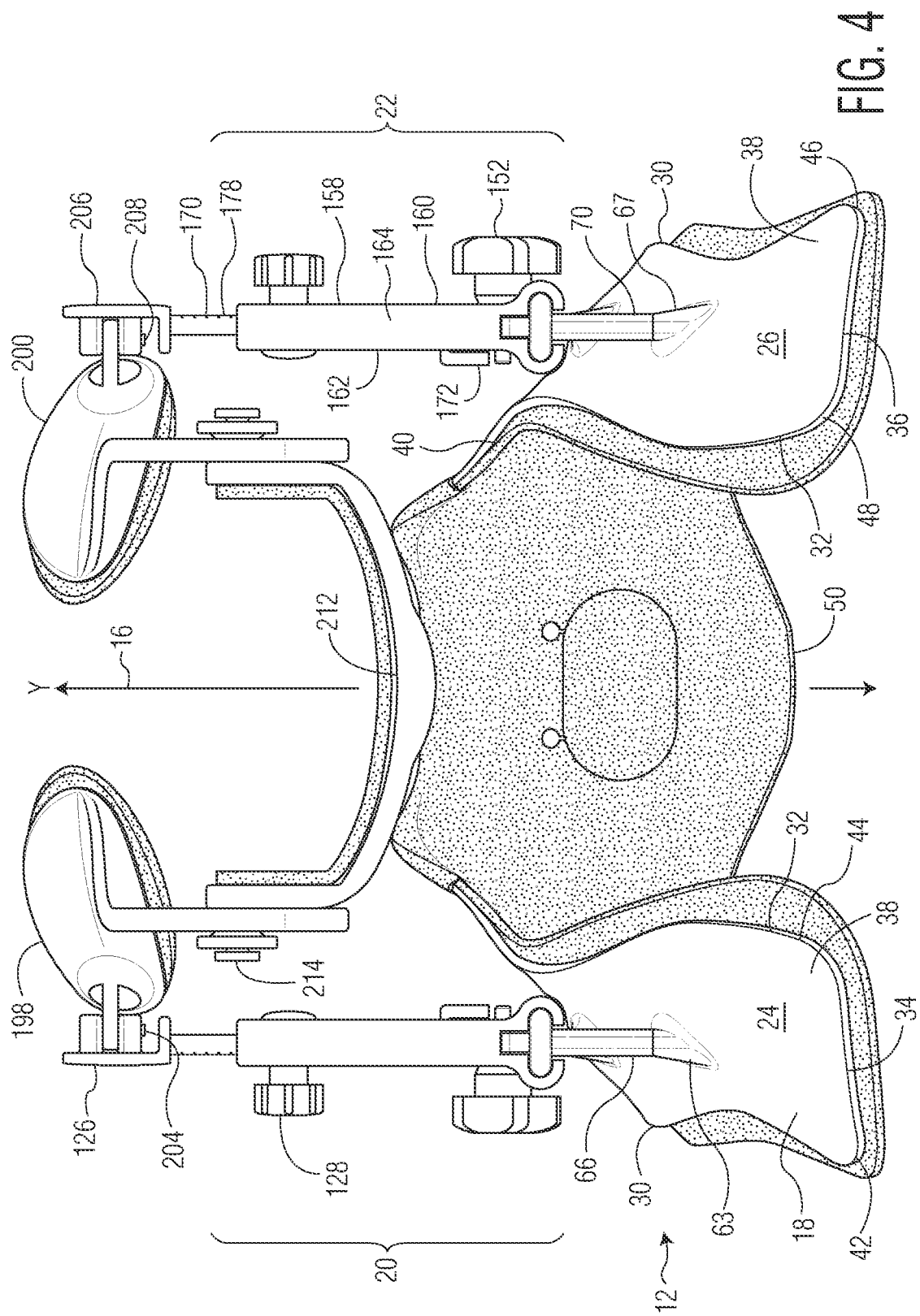
FIG. 4 is front plan view of the collar shown in FIG. 2, further illustrating the bilateral symmetry of the components of the first and second assemblies, relative to an adjustable lordosis displacement assembly.

The collar 10 is symmetrical relative to an axis that coincides with the longitudinal Y-axis of the individual wearer. It should be understood that the collar 10 is being described in a hypothetical setting, in which the body of the wearer is positioned in an anatomically appropriate position with the palms facing outward (not shown). When the body is in the anatomical position, the longitudinal axis (in the Y-axis direction) extends from the top of the head to the bottom of the foot, approximate the center of the body. A mid-sagittal plane aligned coextensive with the Y-axis bisects the body vertically through a middle line running vertically from and through the navel to the top of the head. To advantageously use the bisection of the body, as best seen in FIG. 4, the collar 10 is bilaterally symmetrical along a center line 16, thereby forming a first side 20 (to the right of the center line 16) and a second side 22 (to the left of the center line 16). The terms "right" and "left" are used for purposes of describing the collar 10 relative to how it would be mounted to an individual wearer in an anatomically normal position. Using standard anatomical position terminology for locating components of the collar 10 will reduce confusion and avoid ambiguity. Anatomical terms are well understood by those in the health and medical fields.

Those of ordinary skill in the medical field will appreciate that the terms "forward" and "back" are often misused when applied to flexion and extension motion of the head. As described herein the reference coordinate system is one wherein the X-axis extends right to left in the frontal plane, the Y-axis is the vertical axis, and the Z-axis resides in the front to rear plane. The present invention is concerned with translational movement along of the Z-axis (front to rear or anterior to posterior). This contrasts to much prior art as exemplified e.g. In such representative prior art as Bonutti U.S. Pat. No. 6,770,047, which is concerned with rotational movement about the x axis (flexion and extension, namely looking up or down). See, e.g. FIGS. 4 and 5 of Bonutti. The exemplary prior art Bonutti invention is designed to stretch the neck in flexion (negative x direction, see FIG. 4), or in extension (positive x axis direction, looking up, see FIG. 5) The patient can control this motion by an adjustable control knob located at their naval area, whereas in the present invention the control knob is in the neck area and causes a completely different motion. The present invention thus has a neck brace that moves forward (positive Z-axis) and rearward (negative Z-axis). There is no flexion or extension motion. The object of the present invention is to correct cervical lordosis breakdown at specific areas and to correct forward head translation.

Figure 5:
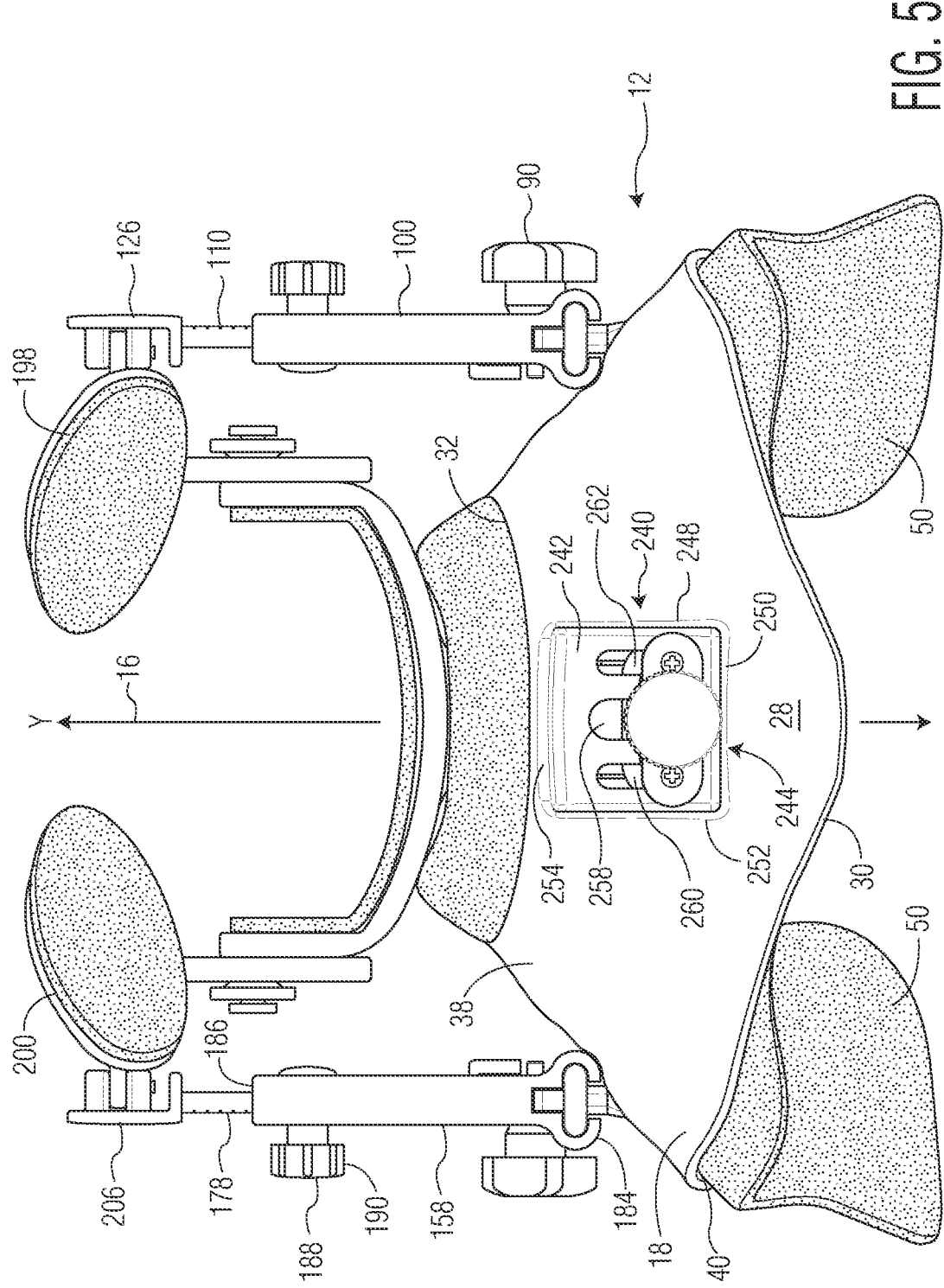
FIG. 5 is a rear plan view of the collar shown in FIG. 4.

FIGS. 4 and 5 further illustrate the structure of the collar 10. The collar 10 is bilateral in the sense that it has a pair of opposed sides that are mirror images of the other, when view along a mid sagittal line (or Y-axis) that divides the collar 10 into two complementary halves. The structure of the collar 10 takes advantage of the bilateral symmetry of the human body, face and skull, with elements that engage the right side and elements that engage the left side of the head in an anatomically normal position. The right side of the collar 10 will engage the parts of the body, head and skull on the right side of the wearer and the left side of the collar will engage the parts of the body, head and skill on the left side of the wearer. As used herein, the term "wearer" refers to any individual who has occasion to use the collar 10, whether or not the wearer is a patient of a health care provider, in an occupational setting, or is using the collar 10 on his or her own accord.

Use of the symmetrical attributes of the components of the collar 10 facilitates a therapeutic correction of FHP or FHT through progressive and incremental adjustments of the position of the head relative to the shoulders. The adjustments help to restore the lordotic curvature of the spine which, in turn, relieve pressures and pain the wearer may be experiencing and reduce impediments normal functions of the body, such as in the respiration or musculoskeletal system.

As shown in FIGS. 4 and 5, the support structure 12 of collar 10 has a first side 20 and a second side 22 that are mirror images of each other relative to centerline 16. Center line 16 divides the collar 10 into bilaterally symmetrical halves. At the foundation of the collar 10 lies the support structure 12. The support structure assembly 12 serves as a support member 18 that is shaped and dimensioned to rest on the shoulders of the wearer when the collar 10 is used. The support member 18 is defined by a pair of outwardly extending arms 24 and 26 which are flexibly joined together in cantilever fashion at a rear back base 28. Rear base 28 forms the back support of collar 10 which creates the proximal end from which arms 24 and 26 extend. Each arm 24 and 26 has respective distal free ends that terminate at the front of the collar 10. The size and shape of the arms 24 and 26, together with the rear base 28, further define the size and length of the support member 18.

Support member 18 is a relatively flat but thin shoulder pad with at least one edge that is preferably anatomically shaped and dimensioned to wrap around a portion of the shoulders and neck areas of the body. As best seen in FIGS. 1, 4 and 5, the shape of support member 18 is defined by an outside edge 30 and an inside edge 32 which terminate and are jointed together at free distal ends 34 and 36, respectively, which further defined the distal ends of arms 24 and 26, respectively. The space intermediate edge 30 and edge 32 define the width of the support member 18, along with a outer surface 38 and an inner surface 40 of support member 18. As illustrated in FIGS. 4 and 5, the outer surface 38 and inner surface 40 of the support member 18 are curved to approximate roughly the likely anatomical shape of the body of the hypothetical wearer.

As best seen in FIG. 4, the free distal ends of arm 24 and arm 26 are each disposed at a slight angle. The corner 42 of arm 24 is oriented at an approximate 0° and faces an opposite corner 44 that is angled about 1-5° higher than corner 42, thereby defining the free end 25 of arm 24. The corner of 46 of arm 26 is oriented at an approximately 0° and faces an opposite corner 48 that is angled about 1-5° higher than corner 46, thereby defining free end 27 of arm 26. Disposing the free distal ends of arms 24 and 26 at an angle helps to approximate the natural curvature of the clavicle areas of the anterior side of the body of a hypothetical wearer so that the collar 10 will rest comfortably on the wearer.

Figure 7:
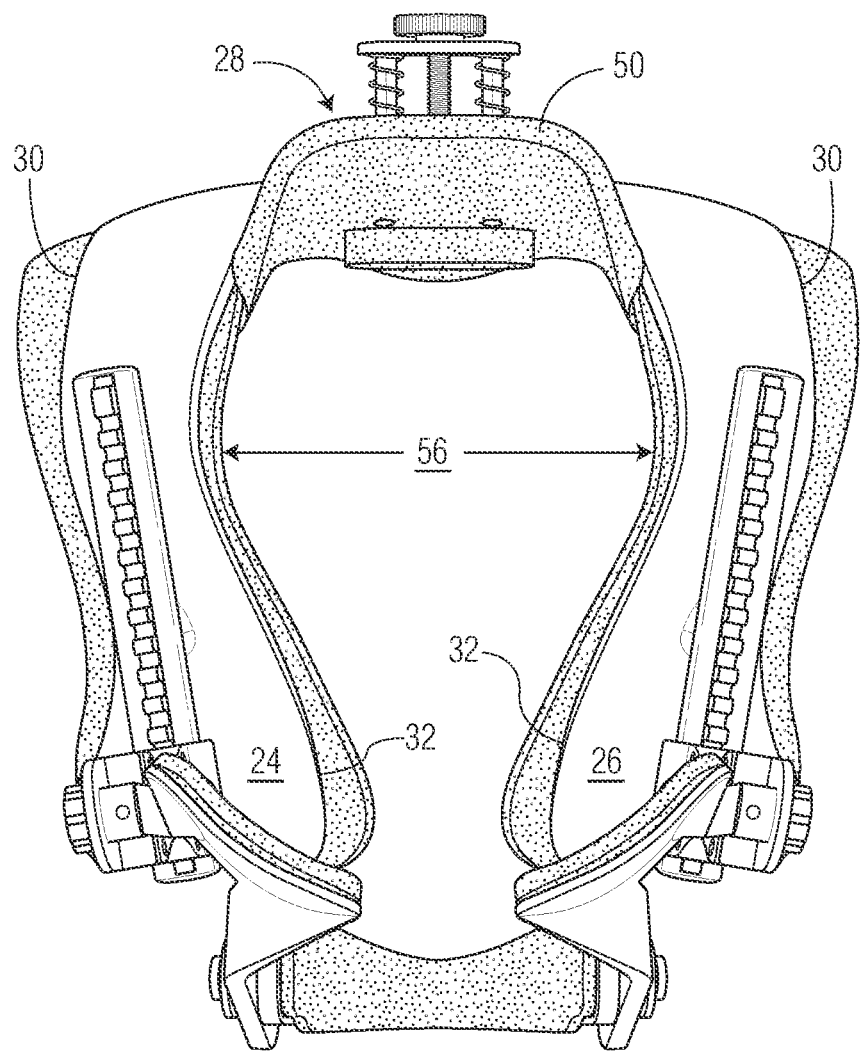
FIG. 7 is a top view of the collar shown in FIG. 2, in a first condition having an opening to receive the head of the wearer.

As best seen in FIGS. 4, 5 and 7, moving from the right side 20 of the collar 10 to the left side 22, the support member 18 extends from the free distal end of the right arm 24 and then becomes progressively disposed in planes that angle from roughly 0° to 5° to roughly about 90° when it is joined at the rear base 28. From the rear base 28 the support member 18 becomes progressively disposed in planes that angle from roughly 90° to about 0° to 5° when it terminates at distal free end of arm 26. The progressive angling of the support member 18 follows the normal anatomical surface of the body starting from the right clavicle, extending posteriorly over the shoulder until it wraps around the neck at the posterior of the body and then extending anteriorly over the left shoulder toward the left clavicle. The natural shape of the support member 18 relative to the shape of the body is advantageously used to rest the collar 10 on the shoulder of the body when the collar 10 is mounted on the wearer in a fully assembled condition. The shape of the support member 18 distributes the load of the collar 10 symmetrically by the shoulders of the body.

Figure 6:
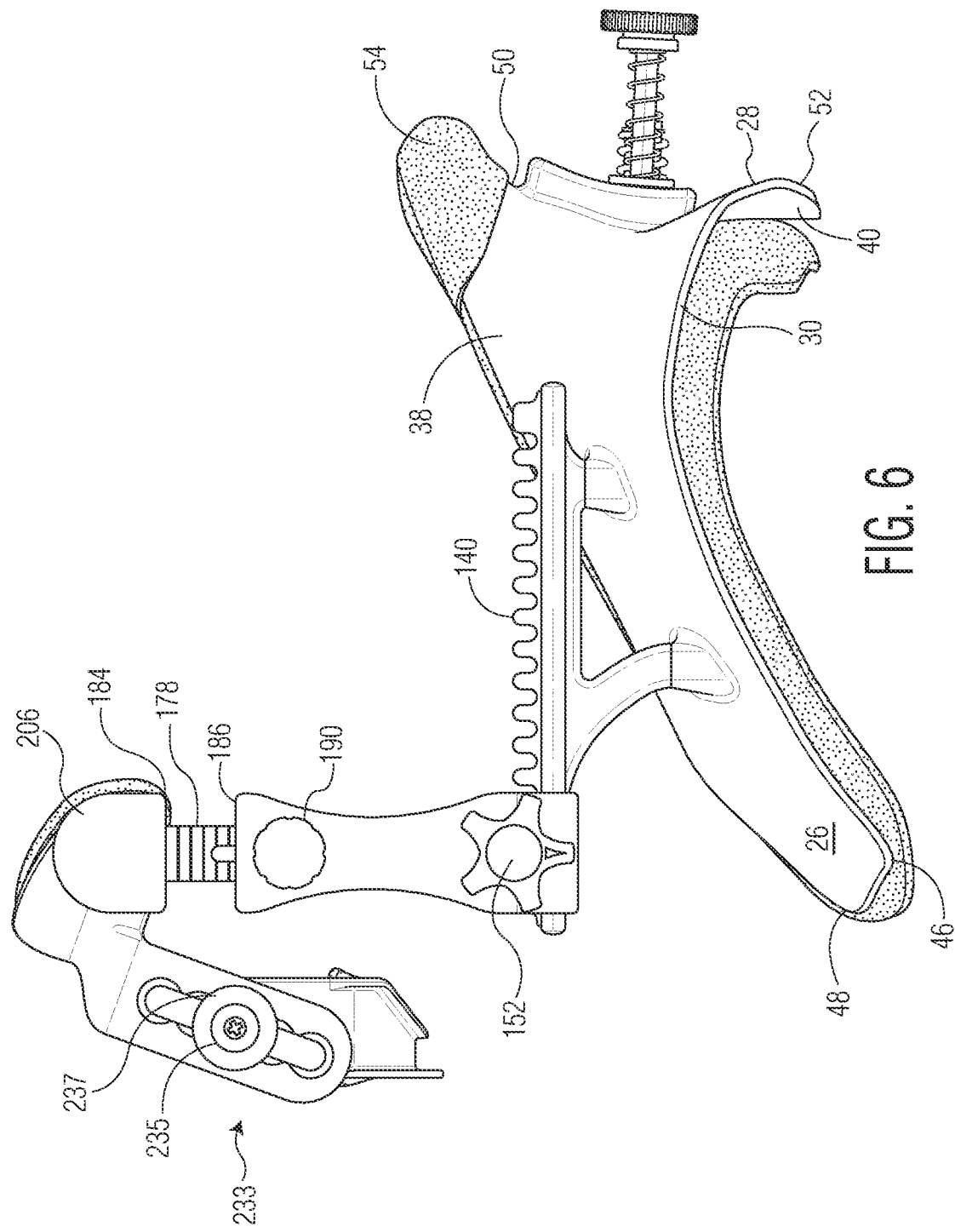
FIG. 6 is an isolated side view of the collar shown in FIG. 2, showing the second side of the support structure and the adjustable structure, relative to an adjustable lordosis displacement assembly.

As best seen in FIG. 6, the rear base 28 is curved to accommodate the shoulder and neck of the body, preferably forming a slight elongated "C" with edge 50 and edge 52 forming the opening of the "C" that cases the right side of the paper. Edge 50 is curved and shaped cover the posterior side of the neck and to capture in cup-like fashion an support the occipital lobe of the head when the collar 10 is mounted on the wearer and will prevent overextension of the cervical spine by the head moving too far aft. The bottom of the rear base 28 terminates at edge 52 which coincides with right edge 36.

Figure 3:
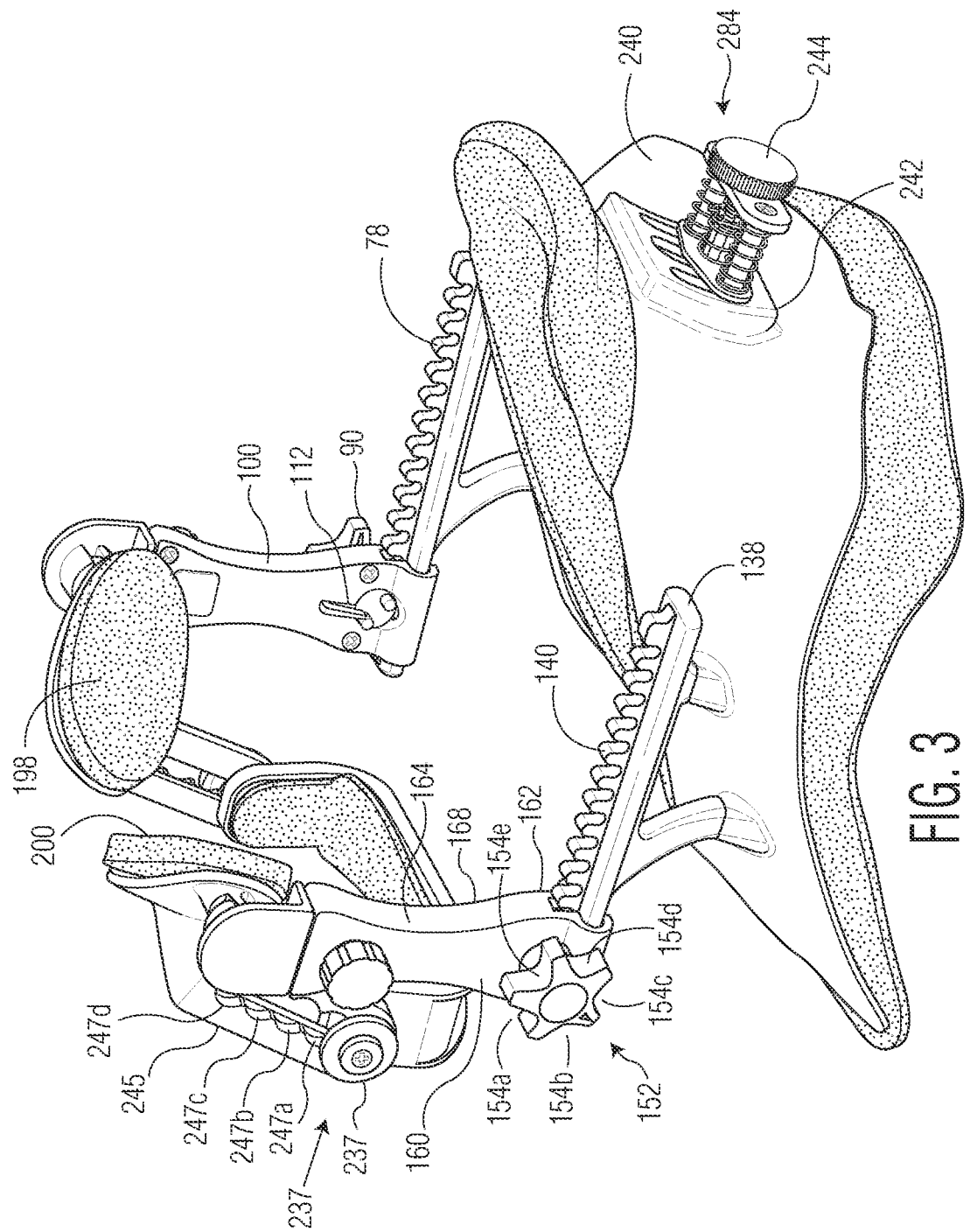
FIG. 3 is a rear perspective view of the collar shown in FIG. 2.

Returning to FIGS. 2 and 3, a comfort pad 54 covers the interior surface 40 of the support member 18, with a portion covering in cup-like portion of the upper neck free end 50 portion of the collar 10. Pad 54 softens use of the collar 10 when it is mounted on the wearer to make it comfortable, particularly if the collar is mounted on bare skin. Pad 54 is made from any soft, durable material that will be comfortable when it engages the wearer, whether or not the wear is using a layer or clothing or not. As shown in FIGS. 2 and 3, pad 54 is made from a black foam laminate, faux suede material that is stretchable and is approximately 2 to 5 mm thick. Stretchable fabric with sufficient memory depending on the warp and weft is preferred so that the pad 54 will retain its shape after several uses. Pad 54 can be attached using a number of well-known securing means, such as Velcro, an epoxy, or other industrial securing means known in the art. Velcro is preferred so that the pad 66 can be replaced for relatively low cost after ordinary wear and tear or if the pad becomes contaminated.

Figure 8:
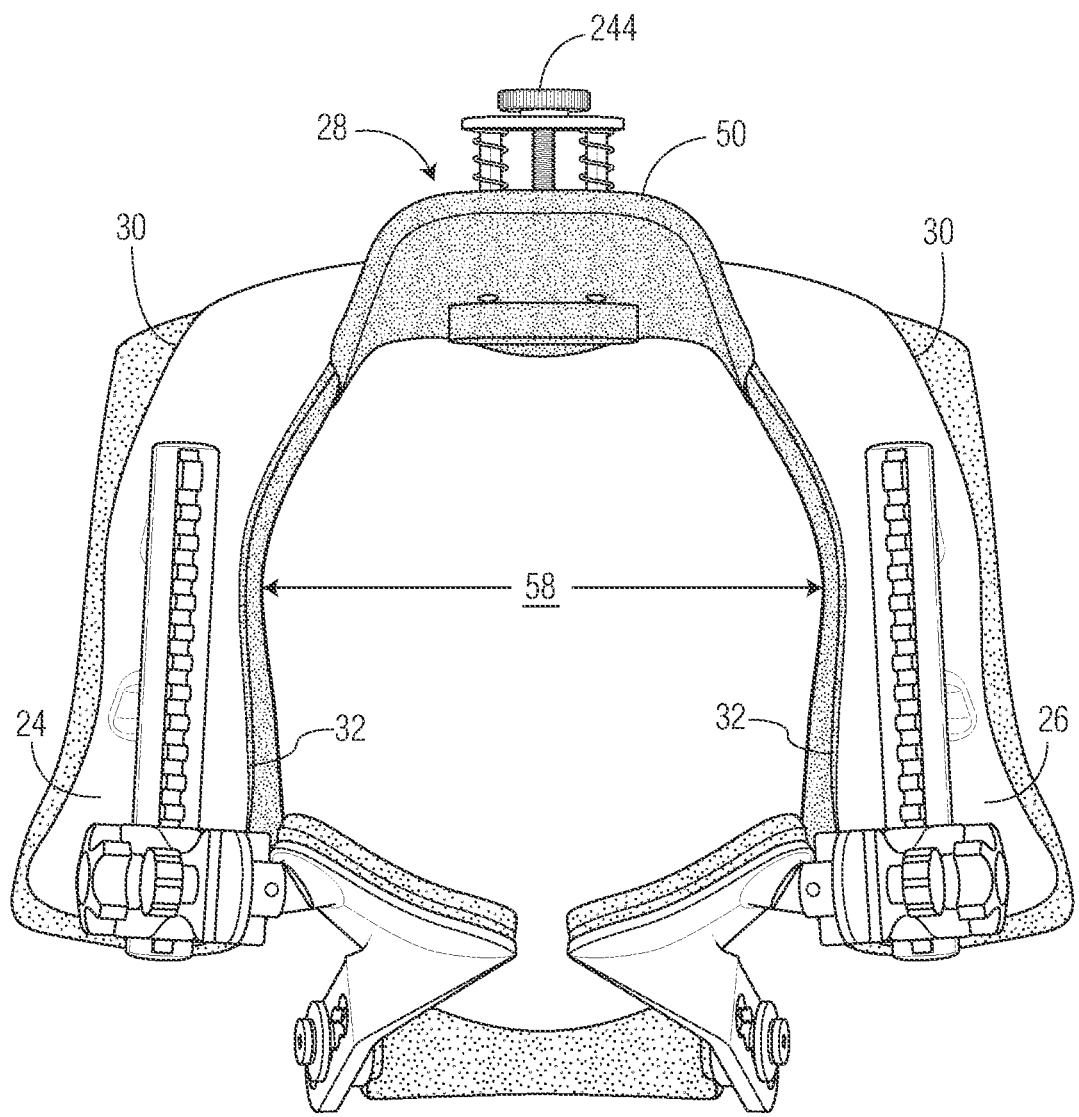
FIG. 8 is a top view of the collar shown in FIG. 7 in a second condition, in which bilateral sides of the support structure are flexed away from each other to increase the size of the opening, thereby enabling the collar to be mounted on or removed from the wearer when the collar is in the assembled condition.

As illustrated in FIGS. 7 and 8, the combination of the cantilever style of the arm 24 and arm 26 are advantageously used to facilitate mounting of the collar 10 to the wearer. It should be understood that arm 24 and arm 26 can be modular or formed as a single unitary molded member with the rear base 28, as shown in FIGS. 7 and 8. It is contemplated that the arms 24 and 26, together with the rear back base 28, can be made using either injection molding, forming, or 3-dimensional printing techniques that are known in the art. Use of a 3-dimensional printing technique can be advantageously use to create a first member to be customized to fit on a given wearer, to fit as closely as possible and match the outward anatomical shape of the wearer. It is conceivable to use three-dimensional scanners, X-ray machines and other imaging equipment can be used either at the medical providers office or at other locations to develop a set of data that will be used to mold or create the first member 12 that is a medically preferred fit over the shoulder and neck areas of the user in a sung fashion. Therefore, it is contemplated that the collar 10 can be of unique design, such that each individual wearer will have a customized collar 10 that is shaped and dimensioned to match the contour for his or her body.

Arms 24 and 26 act in a similar fashion when joined to rear base 28 akin to a living hinge, such that they can be flexed outwardly away from each other relative to base 28. FIG. 7 illustrates the collar 10 in the resting, mounted fully assembled condition as if it is on the wearer. In the resting condition, an opening 56 is formed, which is shaped to approximate the form of the shoulders and neck portion of the body, which the distal ends 34 and 36 will wrap round the anterior part of the body. Flexing arm 24 and arm 26 way from each other increases the relative size of opening 56 to reach opening 58, when has an expanded area. The flex motion of the arms 24 and 26 with their respective distal ends and moving away from each other creates enough space so that the collar 10 can be slid over the head of the individual wearer, until the arms 24 and 26 rest on their respective sides of the shoulders when the collar is in the mounted condition. When the collar 10 is in the mounted condition, the free ends can be released, such that the arms 24 and 26 will return to their non-flexed condition due to the characteristics and memory of the material used.

Returning to FIGS. 1, 2 and 3, the adjustable structure 14 is shown. The adjustable structure 14 is a movable member relative to the support structure 12. The adjustable structure is used to support and move/tilt the head of the individual wearer away from the anterior side of the body to correct undesirable translation.

The adjustable structure adjustable structure 14 is bilateral by design and symmetrical along the hypothetical centerline axis 16 (shown in FIG. 4) of the collar 10 when viewed from the rear or the front. The adjustable structure adjustable structure 14 is fixedly but removably secured the support assembly by a pair of mounting mechanisms 60 and 62 that are formed on opposite sides of arms 24 and 26 of the collar 10. Mounting mechanism 60 is formed by a pair of spaced apart support posts 64 and 66 that can be inserted into mounting stands 61 and 63 which are preferably integrally formed with and extend away from the first side 20 of the right arm 24. Post 66 is distal to post 64.

Opposite to mounting mechanism 60 is mounting mechanism 62, which also includes a pair of spaced apart post 68 and post 70, which can be inserted into mounting stands 65 and 67, respectively, which are formed integrally with and extend away from arm 26. Those of ordinary skill will appreciate that the mounting mechanisms are shaped and dimensioned to be flush with their respective mounting stands to provide an smooth integral appearance. Other means to secure the adjustment structure 14 to the support structure 12 can be used. Both mounting mechanism 60 and mounting mechanism 62 are used as a means to support the adjustable structure 14 and to secure it to the support structure 12 in a sturdy fashion. Because mounting mechanism 60 and mounting mechanism 62 are mirror images of each other, a description of mounting mechanism 60 will be indicative of an apply to mounting mechanism 62.

As illustrated in FIGS. 1, 2, 3 and 4, the adjustable structure 14 is provided which is movable relative to the support structure 12. The second structure 14 enables the wearer or a third party to progressively and incrementally engage a portion of the head of the wearer when the collar 10 is in use, through the use of components that are adapted to capture and rest on the mandible and zygomatic areas of the head, using either a manual operation or, in an alternative embodiment, an automated process. To engage the portion of the face when the collar 10 is in use, the adjustable structure 14 has a first adjustable mechanism 72 and a second adjustable mechanism 74. The adjustable mechanism 72 is positioned on the right side of the collar 10 and adjustable mechanism 74 is positioned on the left side of the collar 10, to form a means for the user to bilaterally and symmetrical adjust the adjustable structure 14 to the preferred mounting condition on the wearer. Because the first adjustable mechanism 72 is a mirror image of the second adjustable mechanism 74, a description of the first adjustable mechanism 72 is representative of the description of the second adjustable mechanism 74.

The first adjustable mechanism 72 is provided to allow incremental and controlled movement forward (anteriorly) and aft (posteriorly) relative to the arm 24. Operation of the first adjustable mechanism 72 is advantageously to adjust and customize the position of the adjustable structure 14 so that the collar 10 can be mounted to and fit on different sizes and shapes of heads of given wearers. The adjustability of the adjustable structure 14 imparts the collar 10 with both uniformity and flexibility to use the collar 10 with numerous individuals, with each having his or her own unique anatomical structure. The ability of the collar 10 to be customized helps reduce manufacturing costs, reduce the costs to maintain different sized collars 10, and provides both the wearer/user and the medical provider to treat the condition of the given wearer because one size does not fit all individuals.

Adjustable mechanism 72 can be operated manually or automatically, depending on the design of the collar 10. As described herein, a manual operation is presently preferred so that the medical provider or wearer can self-control the position of the adjustable mechanism 72 to avoid discomfort and pain. When operated in a clinical environment, the medical provider can achieve the optimal position to impart movement of the head to reverse the effects of forward translation and to return the head it is desired anatomically proper position, such that the ears are roughly situated over the shoulders when the body of the individual has proper posture.

In a preferred embodiment, the adjustable mechanism 72 is formed by a rack and pinion mechanism used as a means that will convert rotary motion to linear motion. As shown in FIG. 2, the rack 76 is mounted to the support structure 12 using the mounting mechanism 60. The rack 76 is a dial-in fixation rail track formed by an inverted "T" bar from which a series or plurality of spaced teeth 78 extend away from a first surface 80. The teeth 78 are positioned on the rack 76 intermediate two opposed sides 82 and 84 that form part of the dimensions of the rack 76.

Figure 19:
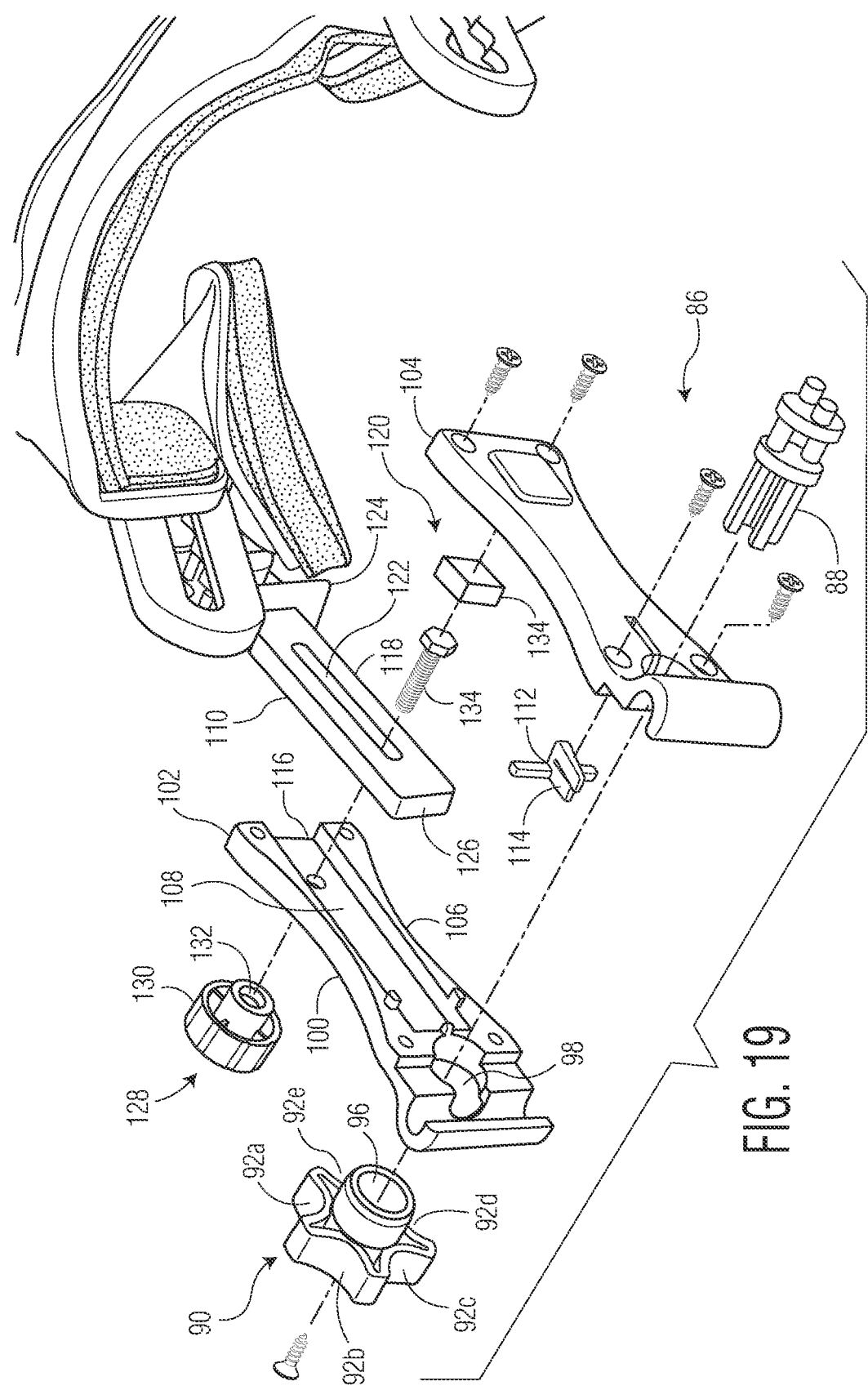
FIG. 19 is an exploded perspective view of the components of the adjustable structure shown in FIG. 2.

As best seen in FIG. 19, a pinion 86 has stepper gears 88 that are shaped to engage the teeth 78 of the rack 76. The gears 88 are provided to rotate in either a clockwise or counterclockwise direction (not shown). As the gears 88 engage the teeth 78 of the rack 72 when they are rotated, the pinion 86 will move in a line that is parallel to the longitudinal axis of the rack 72. Pinion 86 is operated by a knob 90 that has a plurality of thumb receiving areas 92a, 92b, 92c, 92d, and 92e in which an individual can place his or her thumb or fingers to rotate the knob 90 in either a clockwise or counterclockwise direction. Any number of recesses or forms can be used for the knob 90 to allow it to be gripped by the hand of the wearer or a user. It should be understood by those of ordinary skill in the art that a number of equivalent finger or hand operated knobs ban be used as a mechanical means to rotate the gears 88. The knob 90 selected should permit stepwise progressive and incremental movement of the gears 88 to control adjustment of the adjustable structure 14 relative to the support structure 12 when the collar 10 is mounted on the wearer. Controlling the progressive and incremental movement of the adjustable structure 14 will provide the medical provider or user with the ability to limit the amount of adjustment that is necessary to maintain comfort, to avoid pain, and to achieve the desire therapeutic correction of the position of the head.

The rotation of the knob 90 provides a rotational means to allow the gears 88 to operate. The gears 88 extend from a cylindrical base 94 that is fixedly received and secured to a complimentary shaped hole 96 formed in the knob 90. The ability of the knob 90 to be rotated and turn the gears 88 is achieved by inserting the knob into a bore 98 formed within a rigid support post 100. The support post 100 is formed by two complimentarily shaped support members 102 and support 104 that are secured to each other by screws or other securing means. Member 102 and member 104 have a bottom end that are shaped to slide along and to keep the support post movably secured to the rack 76. The bottom of the support post 100 is shaped similar to a pair of hands that join together to form a cup to grasp and slide along the rack 76, thereby keeping the support post 100 engaged. Projecting away from the bottom of the support post 100 is an elongated neck 106 that contains a recess 108 formed by the right support member 102 and left support member 104. Recess 108 forms a channel to receive in telescope fashion a portion of an adjustable support member 110 that will be further described in detail below.

In an assembled condition, rotation of the knob 90 will control the degree and amount of rotation of the gears 88. Because the gears 88 are housed in support post 100, an individual using collar 10 may not know when one of the gears 88 engages the teeth 78 of the rack 76. To enable the user of the collar 10 to sense the step movement of the gears 88 along the rack 76, a flap-type clicker device 112 is used. The clicker 112 has a flap 114 that is made of flexible, but sturdy material such as any polymer based plastic, such as nylon, it being understood that other flexible material with memory to be displaced and return to its resting condition can be used. Preferably, nylon is preferred for its durability and flexibility to engage the gears 88. The flap 114 is pivotably mounted within the housing of the support post 100, so that the flap 114 can be displaced from a resting condition in either in a clockwise or counterclockwise direction to a snap ready condition, in response to engaging one of the gears 88 engaging one of the teeth 78. As the flap 114 is displaced away from its pivotally attached location, the distal end of the flap 114 will move over outer surface of a given gear 88. The memory of the material will cause the flap 114 to snap back to the resting condition, making an audible clicking sound as it clears one of the gears 114 to signal to the user that one of the teeth have engaged the teeth of the track and caused the stepwise movement of the adjustment member 72 along rack 76

As shown in FIG. 19, recess 108 extends along the length of support member 102 and support member 106 and terminates at an opening 116 at the top. The opening 116 is shaped to receive adjustable member 110. Adjustment member 110 is formed by a shaft 118 that is shaped and dimensioned to slide within recess 108 with slight frictional resistance. The shaft 118 includes a position control mechanism 120, which is preferably in the form of an elongated recess 122 that extends intermediate a first end that forms a base 124 and a second free end 126 of the shaft 118. A control mechanism 120 controls the step-wise movement of the adjustable support member 110 relative to the support structure 12 or the rack 76. A stopping mechanism 128 is used to releasably lock and to hold in place the position of the shaft 118 within recess 108, thereby controlling the position of the adjustable support member 110. In a first position, the shaft 118 will be fully inserted into and disposed within recess 108. In the first position, the shaft 118 is said to be in its lowest condition relative to the rack 76. When the shaft 118 is moved in telescope fashion away from the rack 76, a greater distance is achieved, whereby the base end 124 of the shaft 118 is slid into a second position. In a second position, the base end 124 is moved away from the upper end of the neck 106. The length of travel within the shaft 118 controls the position of the base end 124.

Continuing with FIG. 19, stopping mechanism 128 has a knob 130 with a threaded end 132 that receives a threaded screw 134 that is inserted through the recess 122 and a hole formed within the support member 102 to engage the knob 130. Knob 130 will rotate the screw 132, thereby creating a means to convert rotational motion into linear motion and causing a force to urge against the shaft 118 to firmly maintain a given position of the shaft 118 relative to the support mechanism 72. The position of the shaft 118 is locked in place by a bock 134 that receives the head of the screw 132 that is held in place by a complimentary shaped notch from within the second support member 104 that dovetails and interlocks with the block 134. Block 134 prevents further rotational movement of the head of the screw 132. In operation, knob 130 can be rotated to tighten or loosen the screw 132 to increase or decrease the force required to maintain the relative position of the shaft 118 relative to the support mechanism 72. In a preferred embodiment, a series of notches or markings (not shown) similar to a line gauge or ruler that will provide an observable measure of the displaceable movement of the shaft 118 within the recess 108.

The operation of shaft 118 and the adjustable mechanism 72 is representative of the components of adjustable mechanism 74. Adjustable mechanism 74 includes a rack and pinion mechanism, including a rack 138 having teeth 140 projecting away from a first surface 142 that are intermediate a first side 144 and a second side 146. A pinion 148 having stepper gears 150 that rotate along rack 138 for a means to convert rotation motion to linear motion. In much the same way as adjustable mechanism 72, the rack and pinion mechanism of adjustable mechanism 74 is operated by a knob 152 having thumb receiving areas 154a, 154b, 154c, 154d and 154e. Turning the knob 152 will cause the support post 158, formed by a right member 160 and a left member 162. The neck 164 of the support post 158 is elongated and has a recess or channel 168 (not shown) in which a slidable adjustable support member 170 is telescopingly received by the recess 168.

A clicker device 172 is provided to provide an audible sound when the gears 150 engage on of the teeth 140 of the rack 138. The clicker device 172 has similar components to the clicker device 112, and operates by rotational movement of the knob 152. Rotating the knob 152 causes one of the pinion gears 150 to engage one of the teeth 140, which deflects a flap 174 which snaps back to create the audible sound as it is returned to a non-displaced position.

Shaft 178 is provided to be slid through a hole 176 (not shown) that is formed in the top end of the support post 158, which is the entrance to recess 168. The shaft 178 has a first end that forms a base 184 and a second free end 186 (not shown). Adjustment of the length of travel of the shaft 178 within recess 168, relative to the track 138, adjusts the position of the base end 184. The position of the base end 184 can be maintained by operating a releasable locking mechanism 188, which is in the form of a knob 190 that operates a combination screw 192 (not shown) that has a head (not shown) seated within a block 194 (also not shown). The block is nested within the right support member and prevents the screw from rotating further. Rotation of the knob 190 clockwise in typical fashion will subsequently lock the shaft 178 in position. Preferably, a series of spaced notches that are aligned side by side along the longitudinal axis of the shaft 178 can be used for progressive and incremental positioning of the shaft 178 and, by association, the base 186.

As best seen in FIGS. 2 and 4 a head engagement assembly 196 is provided to engage a portion of the head of the wearer so that the head can be displaced relative to the body to correct FHP and translation of the head. The head engagement assembly 196 includes a pair of bilateral and symmetrical adjustable first engagement element 198 (the right side) and a second engagement element 200 (the left side). The first engagement element 198 is pivotably attached to base 126 and the second engagement element 200 is pivotably attached to base 186. The first engagement element 198 and the second engagement element 200 are support and receive a portion of the face of the head of the wearer.

Engagement elements 198 and 200 are preferably cheek pads that are configured so that they can comfortably receive a portion of the zygomatic or maxillary region of the face (namely the cheek bone), which is typically curved. Because the face of many individuals may differ, the position of the members 198 and 200 relative to the face of the wearer are adjustable based on movements of shafts 118 and 178, respectively. Engagement element 198 is pivotably attached on one side to a support member 202 using a pivot pin 204. The pivot attachment enables the free end engagement element 198 to pivot or swing at its attached end toward or away the rear of the collar 10. In a similar fashion, engagement element 200 is attached at one end to a support member 206 by a pivot pin 208, which enables the free end of engagement element 200 to pivot or swing toward the rear of the collar 10. Those of ordinary skill will appreciate that the engagement elements 198 and 200 are spaced apart from each other to permit enough swing of their respective free ends and to accommodate other facial bones of the head of a hypothetical wearer. Additionally, free movement of the members 198 and 200 will accommodate changes in the facial muscles, such as when an individual wearer makes facial expressions like a smile, chews food, or speaks, as three examples, which causes facial muscles surrounding the cheek bone such as the zygomatic (major and minor) and buccinators muscles. The goal is to maintain relatively continuous contact of the engagement elements 198 and 200 with the face of the wearer without experiencing significant loss of contact pressure against the face, which would otherwise diminish the ability of the collar to assert a force to change the position of the head of the wearer, relative to the first member of the collar 10.

When the head engagement assembly 196 is used, the user will turn knobs 130 and 190 counterclockwise to release their associated shafts. Turning knob 130 releases shaft 118 disposed within recess 122 and turning knob 190 releases shaft 178 within recess 182. The wearer or a third party user can pinch the top end 126 and separately pull the shaft 118 away from the rack 76 to adjust the height or position of the engagement element 198. The top end 186 of the shaft 178 can also be pulled away from rack 140 to position the engagement element 200. Once the correct position is determined, knob 130 can be rotated to tighten against the post 100 to lock the shaft 118 in place and knob 190 can be rotated clockwise to tighten it against post 162 to lock the shaft 178 in place. The locking feature will maintain the position of the engagement elements 198 and 200. It should be understood that other position locking means can be used that are equivalent use of a knob 130 and the slidable shaft. As one example, a spring-loaded ball lock pin mechanism can be used. When a button is pressed, the button activates a spring mechanism inside the pin which releases a ball lock. The release of the ball lock will allow another member, such as shaft 118 to move relative to the support post 100, to adjust the position of the engagement element 198. Any mechanism that can maintain the position of the engagement element 198 can also be used. Preferably, the engagement elements 198 and 200 are padded to make they more comfortable.

Once the engagement element 198 and engagement element 200 are in the desired anatomic position and locked in place, they will receive portions of the face. Making further adjustments to shaft 118 and shaft 178, is used to positon the engagement elements 198 and engagement element 200 in the work in cooperation to urge the head of the wearer toward the rear and upward in a lifting or tilting manner by putting pressure on the cheek bones. This movement along the Y-axis and/or the Z-axis will cause the head to begin to translate posteriorly and tilt toward an anatomically desired position, which is advantageously used to correct the forward head posture and cervical lordosis.

Aiding in the movement of the face is a mandible support rest 212. The support rest 212 is adapted to lift the mandibular portion of the head of the wearer away from the chest and to assist in translating the head along the Y and/or Z-axis. The rest 212 is shaped to cup and receive the chin of the wearer. The rest 212 has a first side that is pivotably joined to adjustment shaft 118 and a second side that is pivotably joined to pad 198 and pad 200.

Preferably, the rest 212 is configured as a U-shaped member that is shaped liked the curved cup of a hand that will capture part of the lower portion of the face, including the mandibular prominence that is formed by the lower front of the mandible. The mandibular prominence forms part of the chin of the head, which is can be captured and engaged by the rest 212. The purpose of the rest 212 is to capture the mandibular portion of the head and to urge it in a direction away from the chest of the wearer to return the head as close as possible to the preferred anatomic position when the body will be aligned with good posture, with the ear roughly over the shoulder.

The position of the rest 212 is controlled by a pair of opposed adjustable spring loaded pull assemblies 214 and 216 that will maintain the position of the rest 212 toward or away from their associated face engagement elements 198 and 200. The rest has a opposed sides 218 and 220 that are joined by chin piece 222. Side 218 supports spring loaded pull assembly 214, which includes a pull-pin that creates a snap fit, locking mechanism when seated within a guide member that depends away from engagement element 198. Pull pin assemblies 214 and 216 are mirror images of each other. Therefore, a description of pull pin assembly 214 is representative of pull pin assembly 216.

Figure 16:
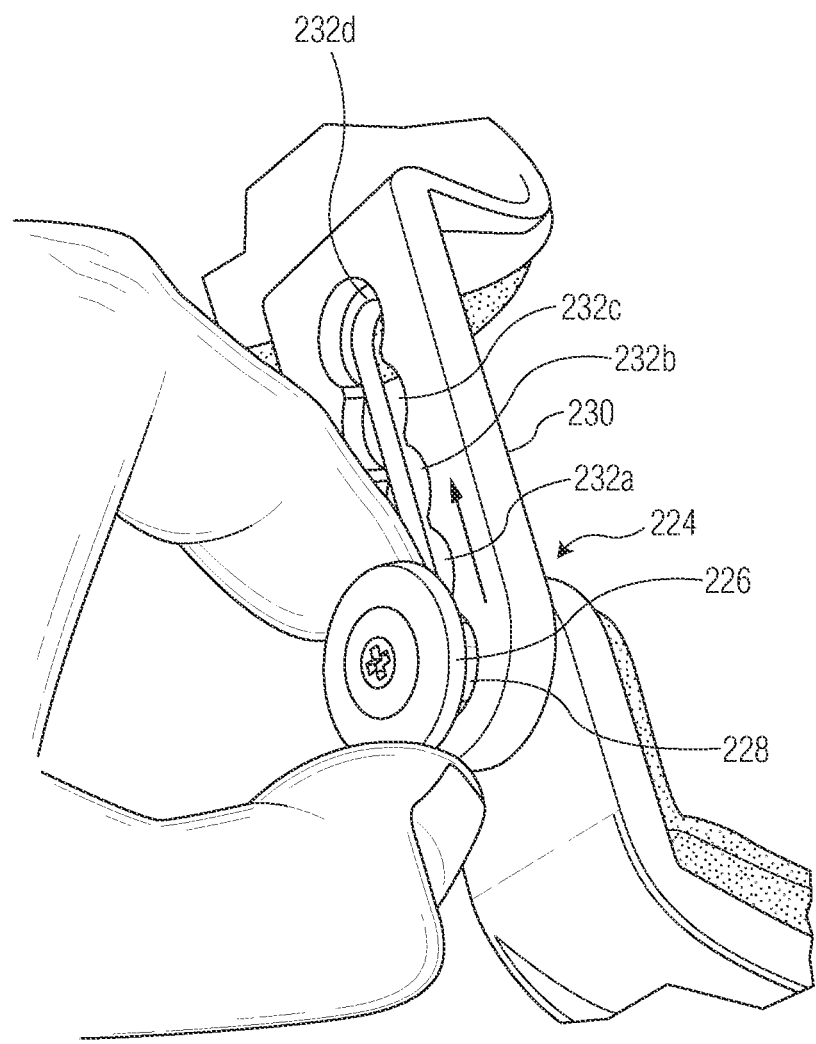
FIG. 16 is an isolated perspective view of a portion of the components shown in FIG. 15, illustrating how the adjustable structure can be adjusted.
Figure 17:
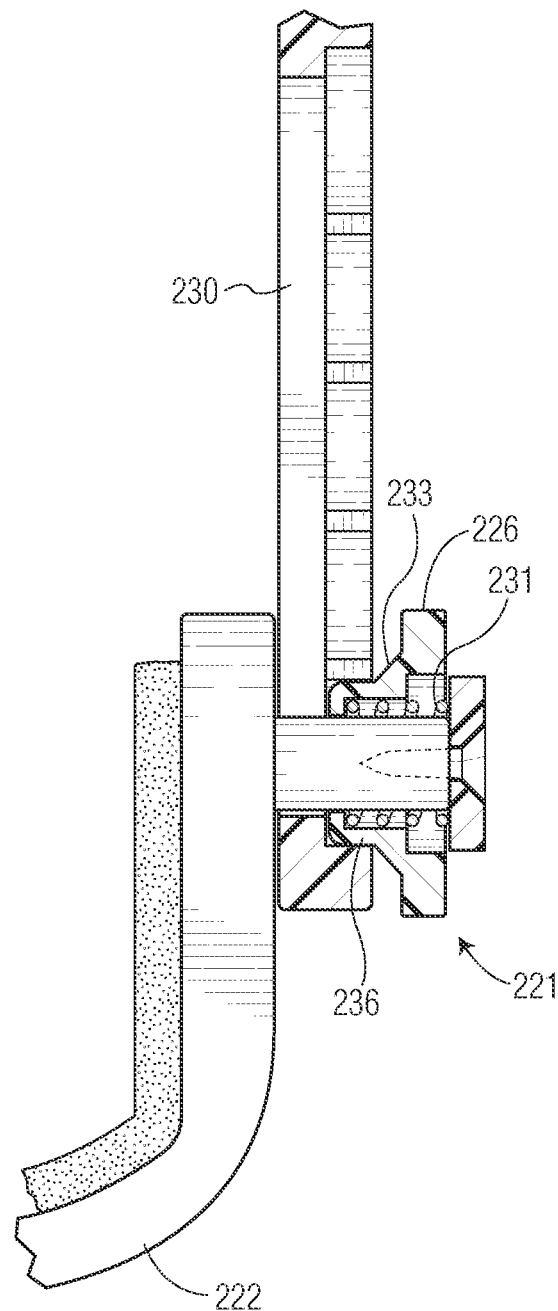
FIG. 17 is an isolated cutaway view of the components of the adjustable displacement assembly component shown in FIG. 15, taken along line 15-15.
Figure 18:
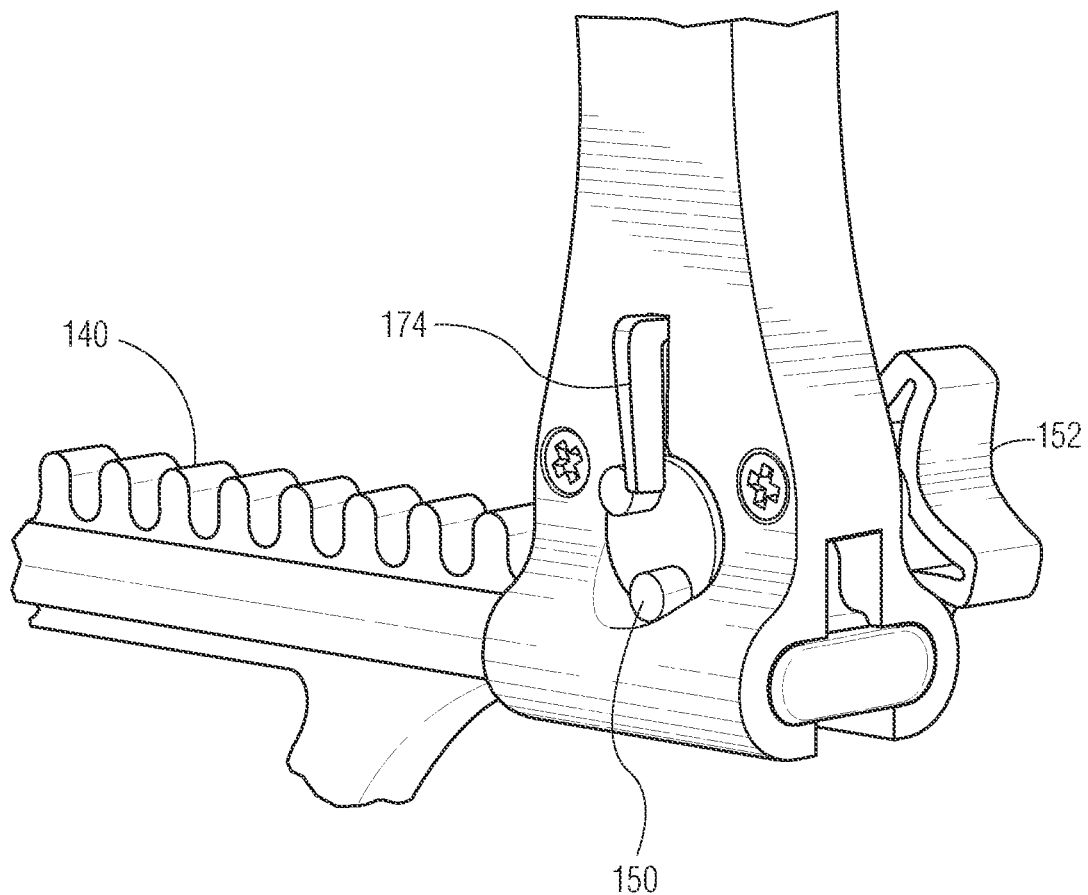
FIG. 18 is an isolated perspective view of the second side of the adjustable structure.

As shown, spring loaded pull pin assembly 214 includes a pull pin 224 having a head 226 that seats within a complimentary sized recess in a locking condition. Pulling the head 226 away compresses a compression spring 231 that uses force to urge the head 226 against and locked with a locking mount 233 that slidably fits inside a recess. The extension of the compression spring is achieved by sufficient pulling force by a user, which then frees rod 228 to side 218 along guide member 230 to adjust the position of the support member. Guide member 230 has a one or a plurality of joined recesses 232a, 232b, 232c, and 232d that are spaced next to each other along a line that is parallel to the longitudinal axis of the guide member 230. The recesses 232a, 232b, 232c, and 232d are joined together to form one slideable, snap positioning locking mechanism, in which the spring loaded pull pin 224 will move along a line that is parallel to the longitudinal axis toward and away from the face engaging element 198. As best seen in FIGS. 16 and 17, the pull pin 224 travels in within the track formed by the plurality of recesses 232a, 232b, 232c, and 232d, with each recess permitting a locking engagement of the pin to maintain the position of rest 222. The pin 224 is operated by pulling head 226 away from guide member 230, thereby stretching a compression spring 231 which in turn exposes rod 228. When the head 226 is released, the force of the spring causes the head 226 to snap-back to a locking condition, thereby maintaining the position of the rest 212. The movement of the head 226 is controlled by a stop 236 which is seated within the recess 232a, 232b, 232c, and 232d. Stop controls the movement of the head 226, which includes a beveled portion of head 226 that fits within the recesses in dovetail fashion to keep the head 226 in place. Other equivalent adjustable locking means can be used that are known in the art.

A similar spring loaded pull assembly 233 is used for the left side of the collar 10. In much the same way as spring loaded pull assembly 214, pull pin assembly 233 includes a pull pin 235 that has a head 237 that will seat within a complimentary sized recess in a locking condition. Pulling the head 237 expands a compression spring 239 (not shown) that uses force to urge the head 237 against and locked with a locking mount 241 (not shown) that slidably fits inside a recess. The extension of the compression spring is achieved by sufficient pulling force by a user, which then frees rod 243 to side along guide member 245 to adjust the position of the support member. Guide member 245 has a one or a plurality of joined recesses 247a, 247b, 247c, and 247d that are spaced next to each other along a line that is parallel to the longitudinal axis of the guide member. The recesses 247a, 247b, 247c, and 247d are joined together to form one slideable, snap positioning locking mechanism, in which the spring loaded pull pin 235 will move along a line that is parallel to the longitudinal axis toward and away from the face engaging element 200. The pull pin 235 travels in within the track formed by the plurality of recesses 247a, 247b, 247c, and 247d, with each recess permitting a locking engagement of the pin to maintain the position of rest 212. The pin 235 is operated by it away from guide member, thereby stretching a compression spring 239 which in turn exposes rod 243. When the head of pin 235 is released, the force of the spring causes the head 237 to snap-back to a locking condition, thereby maintaining the position of the rest 212. The movement of the head 237 is controlled by a stop 249 which is seated within the recess 247a, 247b, 247c, and 247d. Stop controls the movement of the pin 235, which includes a beveled head that fits within the recesses in dovetail fashion to keep the pin 235 in place.

In a preferred embodiment, the collar 10 comprises an adjustable fulcrum displacement assembly 240 operatively secured to the first support assembly 12. The adjustable displacement assembly 240, in use, will progressively and incrementally apply corrective forces to at least one vertebrae of the wearer. The corrective forces will assist in restoring the curvature of the cervical spine of the wearer to an anatomically desired position though the use of linear force that presses against the neck.

Figure 9:
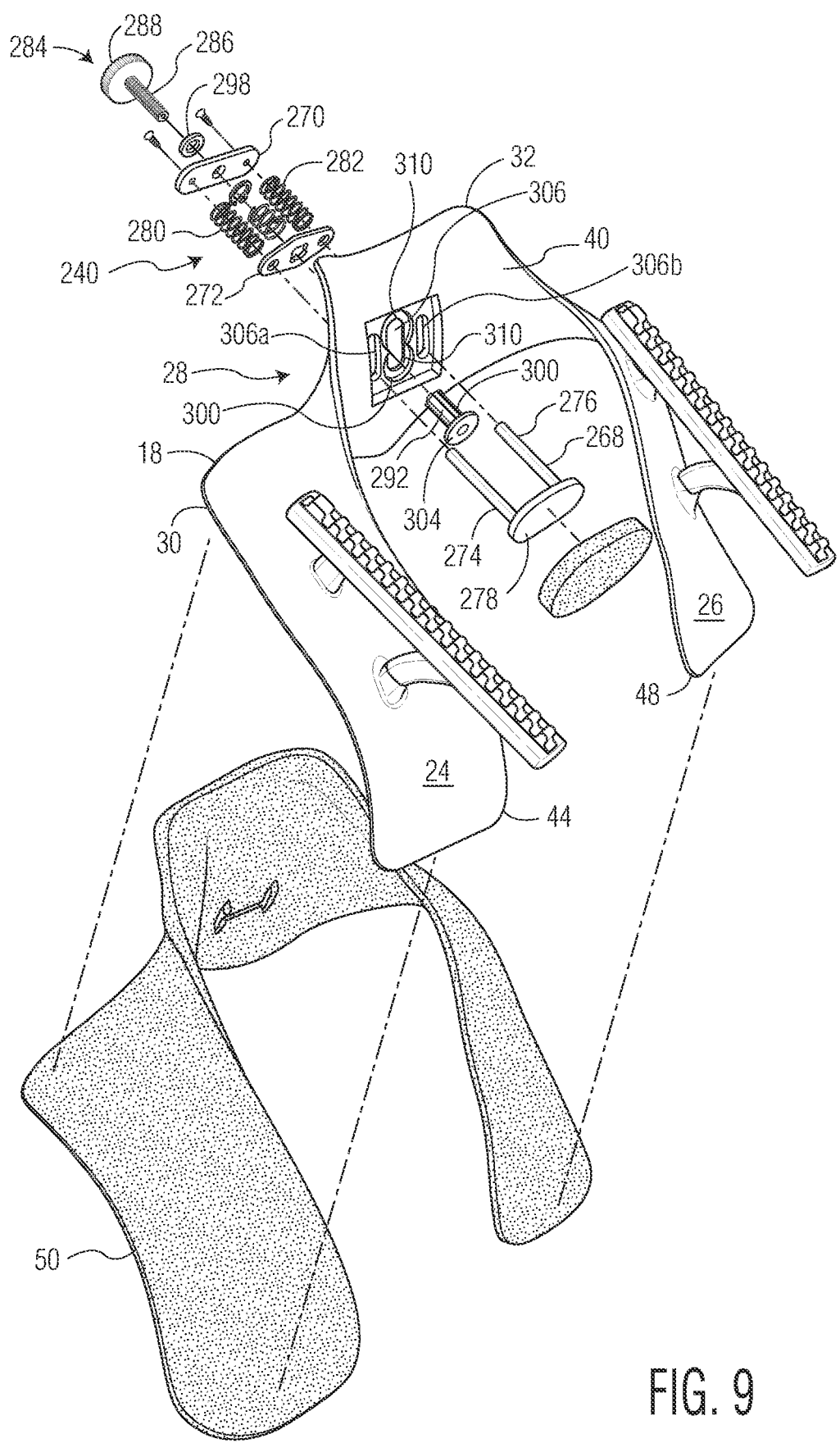
FIG. 9 is an exploded perspective view of the components of the support structure and the adjustable displacement assembly of the collar shown in FIG. 2.
Figure 10:
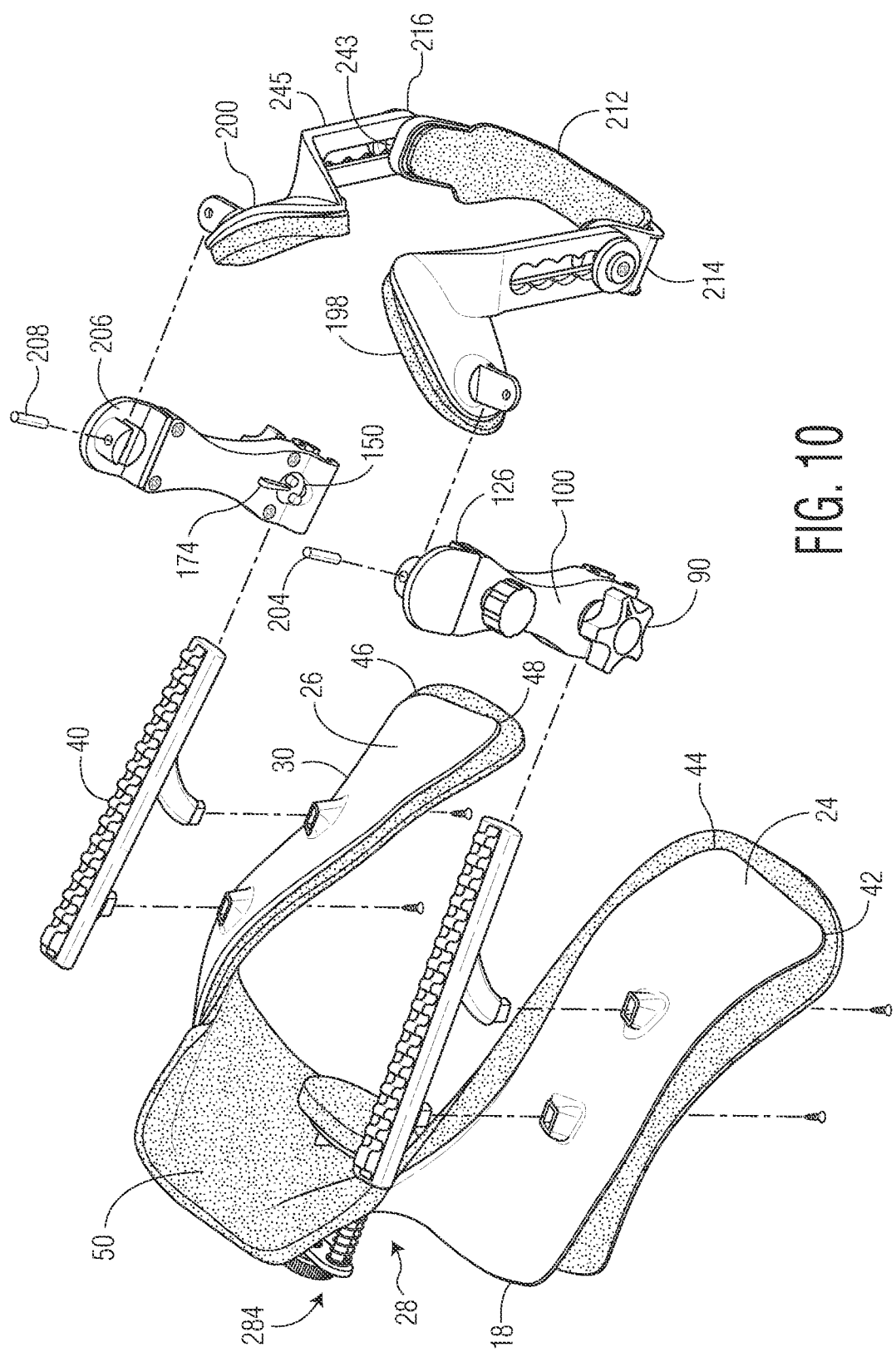
FIG. 10 is an exploded perspective view of the components of the adjustable structure of the collar shown in FIG. 2, relative to the support structure.
Figure 11:
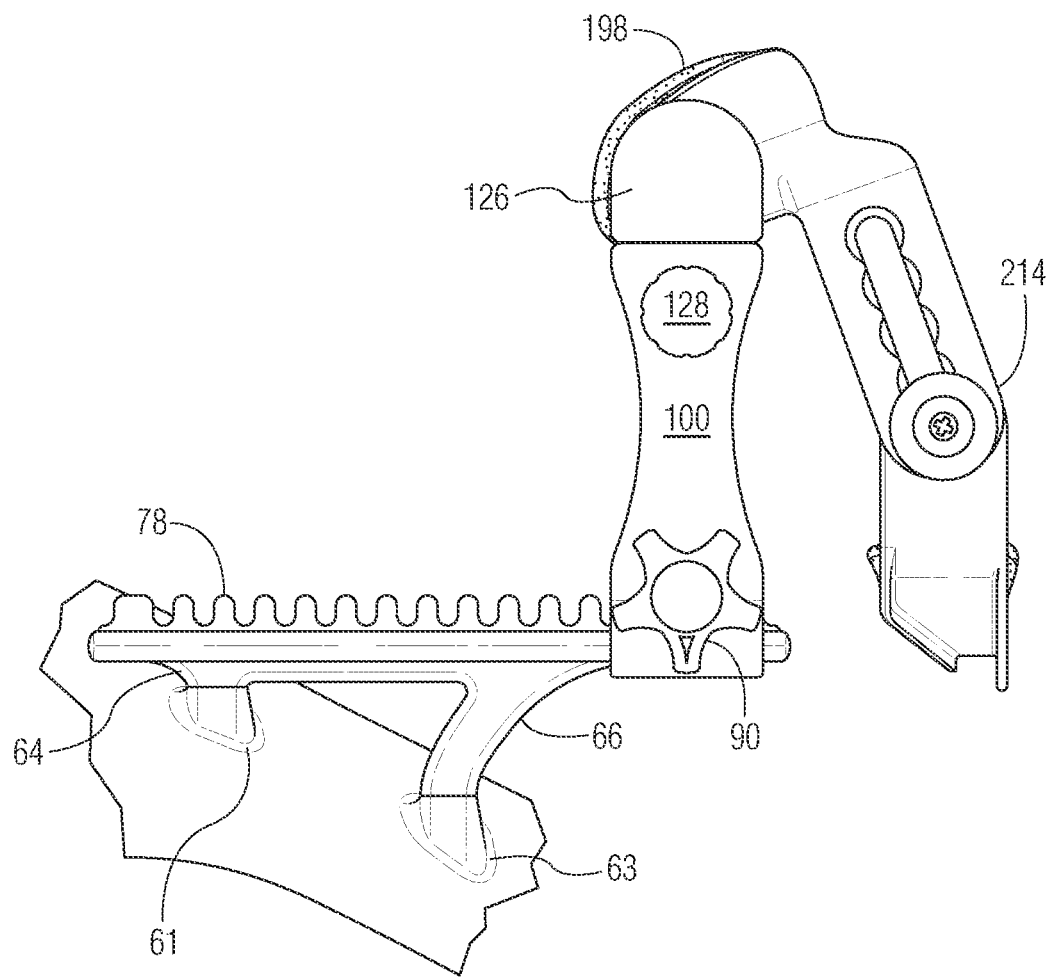
FIG. 11 is an isolated side view of the first side of components of the first and second assemblies shown in FIG. 2, the adjustable structure being illustrated in a first condition.
Figure 12:
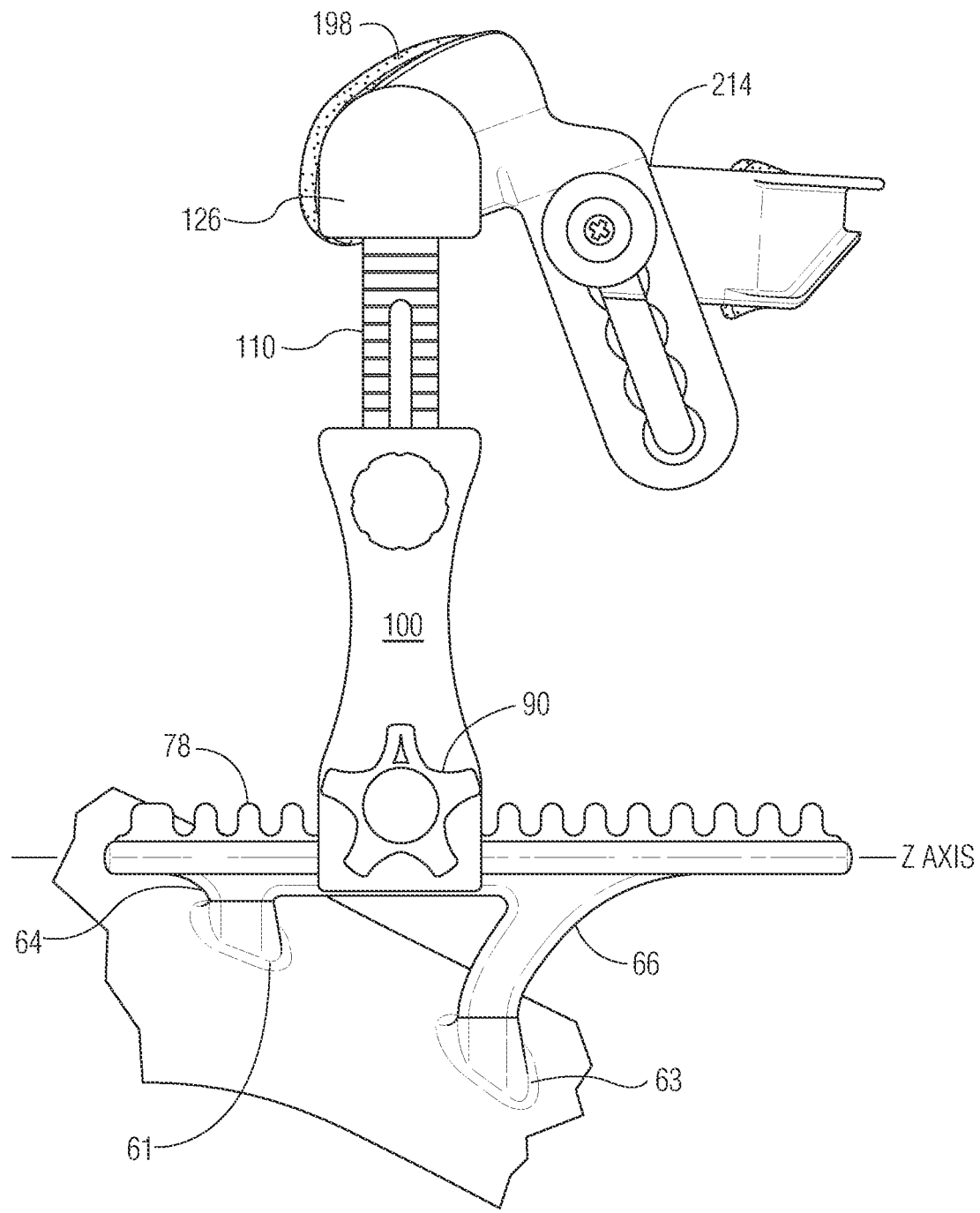
FIG. 12 is an isolated side view of the first side of components of the first and second assemblies shown in FIG. 2, the adjustable structure being illustrated in a second condition.
Figure 13:
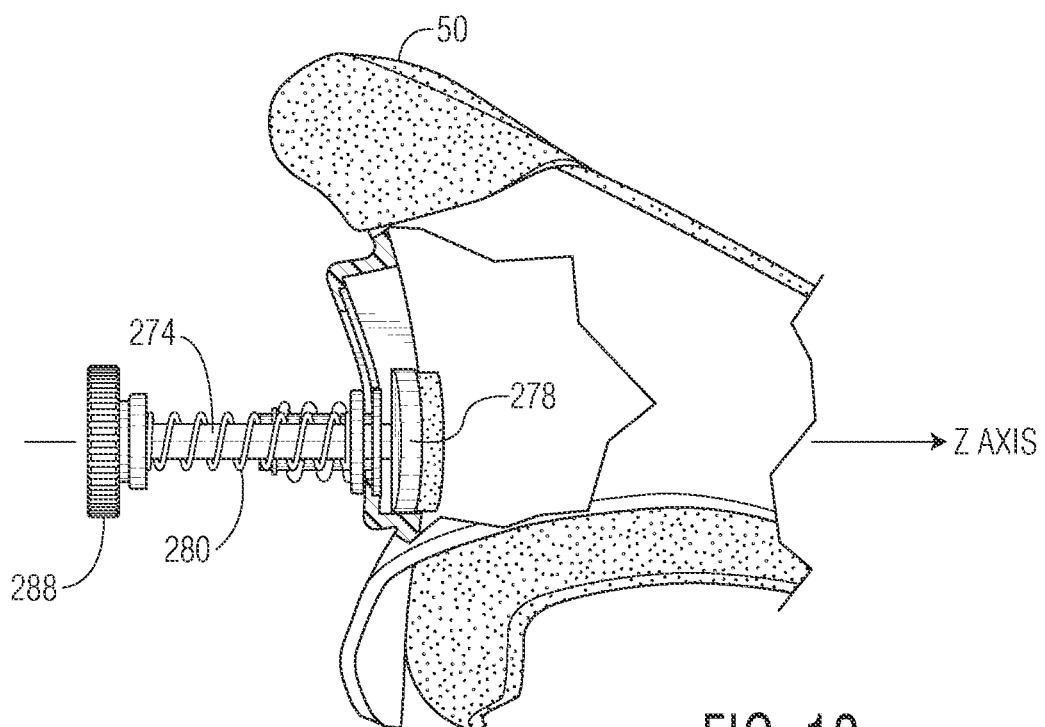
FIG. 13 is an isolated cutaway side view of the adjustable displacement assembly shown in FIG. 4 taken along line 13-13, the adjustable displacement assembly being in a first condition.
Figure 14:
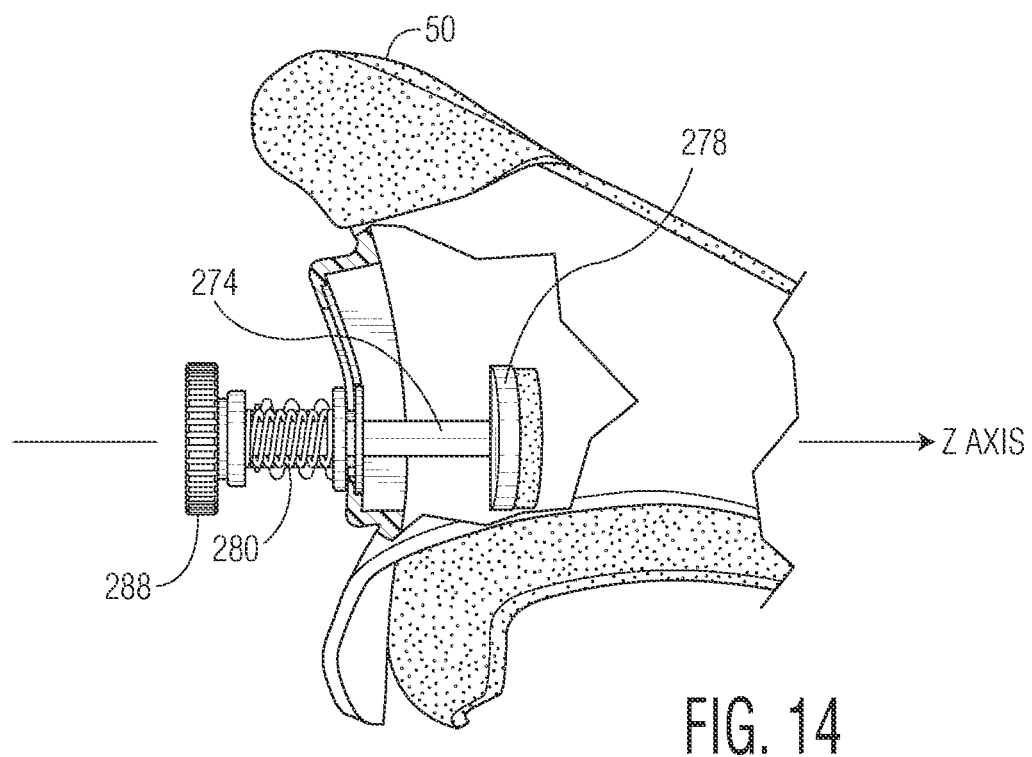
FIG. 14 is an isolated cutaway side view of a portion of the components of the adjustable displacement assembly shown in FIG. 13 in a second condition.
Figure 15:
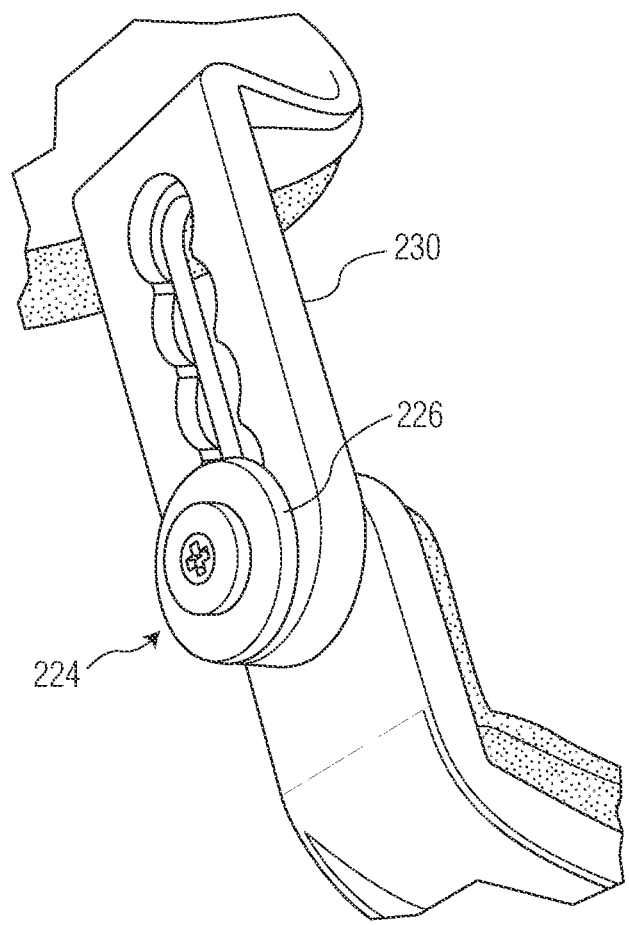
FIG. 15 is an isolated perspective view of a portion of the components of the first side of the adjustable structure shown in FIG. 11, the components being in a first condition.

As seen in FIGS. 3, 5, and 9, the adjustable displacement member 240 comprises a base 242 and a lordosis correction fulcrum assembly 244. The base 242 is secured to or formed integrally with the rear portion of the first support assembly 12. As best seen in FIGS. 6 and 9, base 242 has edge 246 from which sides 248, 250, 252 and 254 depend and join at their corners to further define base 242. As seen in FIG. 3, outside surface 256 is slightly curved in a "C" shape with the opening facing posteriorly. Formed within surface 256 is a least one adjustment slot 258 that operatively receives the fulcrum assembly 244. Preferably, a series of side-by-side slots 258, 260, and 262 are provided to enable step-wise progressive and incremental displacement of the fulcrum assembly 244. Each slot has a first opening that coincides with surface 258 and a second opening that terminates below the inner surface 40 of the support structure 12. Turing to FIG. 9, the second opening of slots 258, 260 and 262 are recessed so that the fulcrum assembly 244 can be displaced into a resting, closed condition that coincides with or is slightly below surface 40. The second opening of slots 258, 260 and 262 guide and control the I movement of the fulcrum assembly 244 relative to the first support assembly 12 along the Z-axis. The movement of the fulcrum assembly 244 creates a force that will engage the back of the neck of the wearer, essentially pushing against the posterior of the neck which about which the head will flex along the Y-axis.

The fulcrum assembly 244 comprises a push style plunger assembly 266 and a translation correction assembly 268 to apply pressure against the neck of the wearer. The plunger assembly 266 is formed by a pair of spaced part flat mounting base plates or washers 270 and 272. A first plate 270 is shaped to engaged and rest on the outer surface 256 of base 242. Positioned above the first plate 270 is a second plate 272, which are in spaced relation to one another and are separated by a pair of guide posts or arms 274 and 276 that are joined to the correction assembly 268.

The correction assembly 268 has a neck engagement member 278 from which guide posts 274 and 276 extend and are attached in cantilever fashion at their proximal end. Posts 274 and 276 are tubular and have internal threads that receive screws that secure the free distal end to the first plate 270. Surrounding each post 272 and 276 are their respective compressions springs 280 and 282 that are positioned intermediate the first plate 270 and the second plate 272. The compressions springs 280 and 282 allow the plates 270 and 272 to be squeezed toward each other, which causes the neck engagement member 278 to move. Therefore, the movement of the plates 270 and 272 create a dynamic and adjustable neck engagement device which operates as a movable fulcrum that displaces along a line parallel to the Z-axis. The distance of travel of the neck engagement member 278 (i.e., the fulcrum) is controlled by the compressive forces in the compression springs 280 and 282, which are applied to and pushes against the second plate 272 to move it away from the first plate 270. The second plate 272 has a fulcrum control guide 284 that will control the position of the second plate 272. The fulcrum control guide 284 is preferably a threaded screw 286 having a knurled knob 288 that is used to operate the screw 286. The screw 286 is received by a threaded key 290 (not shown), which has at least one channel 292 and stop 294 which forms a top end on which a compression spring 296 is mounted. The stop 294 limits the travel of a washer 298 which is advantageously used to limit and control the distance of travel by the screw 286.

The use of threads creates a unitary push type of control guide that is used to operate the position of the neck engagement member 278, which functions as the fulcrum of which the head will pivot about the neck. The combination of threading the control guide 284 into the position pin 300, enables the displacement and position of the neck engagement member relative to the inner surface 40 of the support structure 12 to be controlled and locked into place without appreciable deterioration in the position. The step movement of the position of the neck engagement member is controlled by turning the knob 288, which creates a force in the direction of the base 242.

The adjustment of the neck engagement member 278 along the Y-axis further controlled by a releasable locking mechanism 304. The locking mechanism 304 is a round cap that is adapted to fit in dovetail fashion in a complimentary shaped adjustment guide 306. The adjustment guide 306 is defined by at least one but preferably a series of recesses 308 and 310 (two shown) that are sunken below the outer surface 40 and are joined to one another on one side. Each recess 308 and 310 forms a seat to releasably and matingly receive the cap of the locking mechanism 304 to lock in the position of the fulcrum assembly 244 within the base 242. The locking mechanism 304 is operated by pushing the plunger assembly 266 toward the base 242, which will release the cap from the locking mechanism 304, thus enabling the locking mechanism 304 to be moved from one recess 308 to the other recess 310, thereby adjusting the positon of the neck engagement member 278, relative to the neck of the wearer. Those of ordinary skill will appreciate that adjustment of the position of the neck engagement member 272 is controlled by the slots 258, 260 and 262 and are locked in place by the locking mechanism 304. When the desired positon is achieved, the plunger assembly 266 is released, which permits compressed springs 280, 282 and 296 to extend and cause the snap fit of the cap of the locking mechanism 304 to become securably seated within one of the recesses 308 or 310. The compressing springs 280, 282 and 296 create a reactive force in the direction away from the base 242 which, in turn, maintains a releasable snug fit of the locking mechanism within the recesses 308 or 310. Those of ordinary skill will appreciate that the bottom of recesses 308 and 310 will prevent the channel 302 from moving further within the recessed area of the base 242, and maintains a relatively flush surface between the cap and the inner surface 40 of the support structure 12.

The collar 10 is designed to not only support an injured area, but also improve the cervical lordosis and correct the malposition cranium (i.e. head) that results from FHT and FHP. The collar 10 will correct the malposition by providing negative Z-axis translation of the head to correct forward head translation and the posture of the individual patient. Use of the collar 10 will aid in cervical rehabilitation by applying corrective forces over a desired or prolonged period of time which will expedite the remodeling and rehabilitation of cervical-para-spinal ligaments and discs. Those of ordinary skill will appreciate that the amount of time the collar 10 is required to be worn by the user will depend on a clinical analysis of the how long the corrective forces will need to be applied in order to achieve a return to the desired anatomical posture and cervical lordosis, thereby creating sufficient muscle memory and adjustment of ligaments so that the individual will have improved posture when the collar 10 is not used. The frequency of use of the collar 10 can cover a span of a number of days, weeks or months of use sufficient to eliminate maladies associated with forward head translation or poor posture, such as neck, back pain, respiratory compromise, and weekly migraines, as four examples.

To use the collar 10, the medical provider should first assess the level of FHT and FHP the individual patient is experiencing. A medical provider will perform an x-ray of the individual patient and conduct an exam to determine the degree of the translation of the cervical spine from its normal anatomical position. The medical provider will consider the individual's history, causes of the deformity, physical activities, and the likely cause of the changes to the cervical spine. It is desired to develop data which include measurements of the degree of translation of the head, the degree of extension of the cervical spine, and the posture of the individual patient when viewed from the perspective of the coronal and sagittal planes. The data can be compared with other external data that will serve as a baseline for comparison. The external data will be developed for a hypothetical patient with similar age having a normal range of motion, flexion and extension of the cervical spine, and cervical lordosis.

Figure 20:
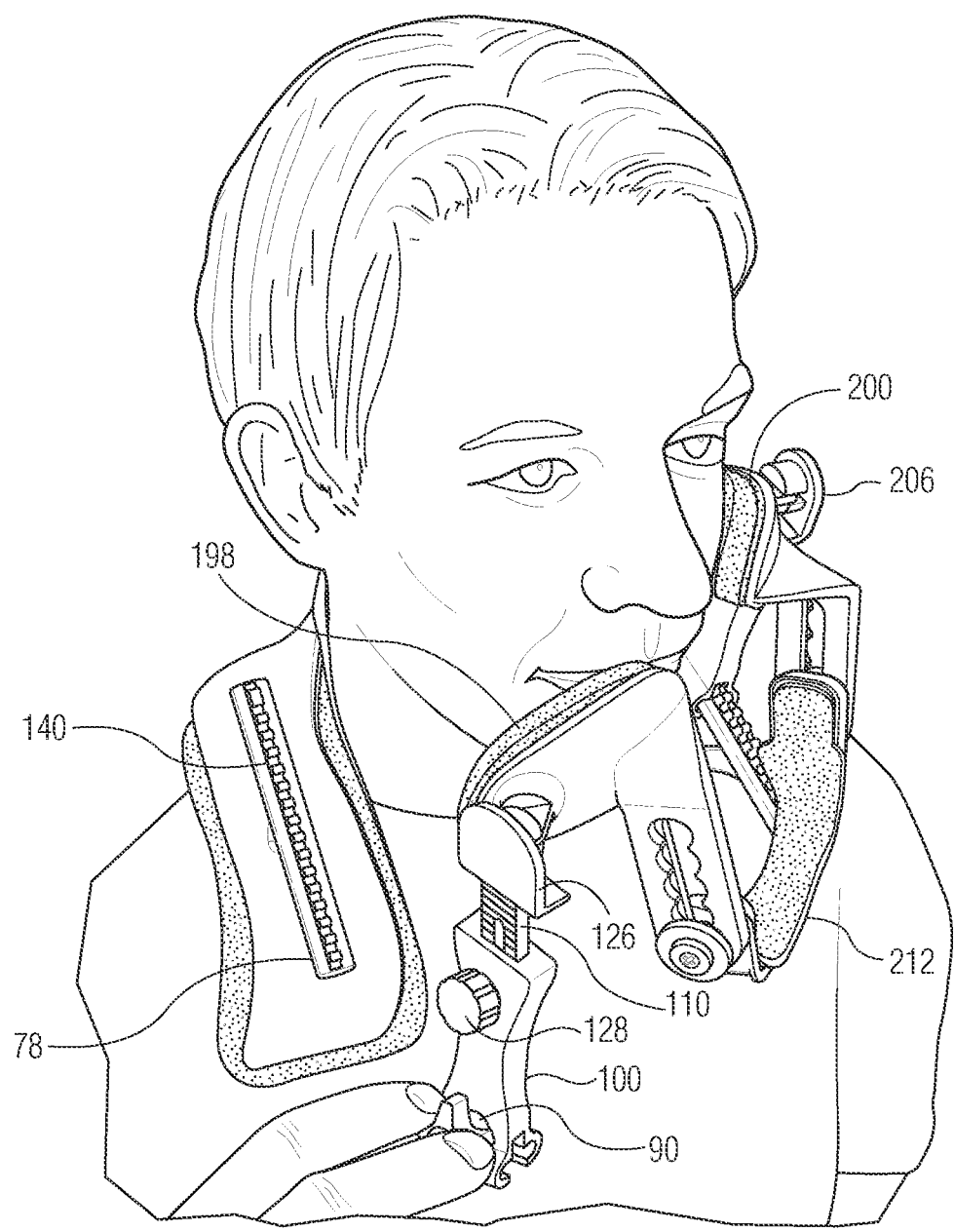
FIG. 20 is a perspective view illustrating one method of mounting the collar shown in FIG. 2 to the body of the hypothetical wearer, the collar being adapted to move intermediate a first condition to a second condition.

One side of the collar 10 is released, such as the right side, by turning the knob 90 in a clockwise direction until the support post 100 is released from the rack 76. Releasing the post 100 from the rack 76, will allow the adjustable structure 14 swing about pivot 208 associated with the left face engagement 200 (i.e., the check pad). The pivoting action permits the adjustable structure 14 to move from a mounted condition as illustrated in FIG. 1 to an open condition as illustrated in FIG. 20. Next, the collar 10 is mounted on the individual wearer, such that right arm 24 of the support member 18 will rest on the shoulder of the right side of the wearer and the left arm 26 of support member 18 will rest on the left side of the individual wearer. The rear base 28 will wrap around the neck and can be used to position the collar 10 in a manner that will be comfortable to the individual wearer. Once the collar 10 is in position, the adjustable structure 14 can be swung to return from the open condition to a closed condition by permitting the pinion 86 to engage the rack 76 and then turning the knob 90 counterclockwise which will move the adjustable means 72 on the rack 76 in a negative Z-axis direction. The knob 90 should be operated so that the adjustable means 72 is aligned with the adjustable structure 74 so that symmetrical, bilateral movement of the adjustable structures 72 and 74 will be in harmony. It should be understood that the adjustment means 74 on the left side can be released, by operating the knob 150 clockwise until the pinion 150 is released from rack 138, which allows the adjustable structure 14 to swing about pivot pin 204, to move the adjustable structure from a first closed condition to a second open condition in which the collar 10 can be mounted on the wearer.

Next, when the collar 10 is in the mounted and closed condition, the adjustment mechanisms 72 and 74 can be adjusted by operating knob 90 and knob 150. Knobs 9 and 150 are rotated counterclockwise or clockwise to positon the adjustable structure 14 so that the chin rest 212 is in position to engage the chin of the wearer. The positon of the chin rest 212 is adjusted by operating the spring button pull assembly 214 and spring button pull assembly 216 so that the chin rest 212 can be move toward or away from the face engagement elements 198 and 200, until the chin rest engages the mandibular portion of the head.

Next, adjustments are made to the face engagement elements 198 and 200. The position of the face engagement elements 198 and 200 are controlled by rotating knob 130 to free movement of adjustable support member 110 and rotating knob 190 to free movement of adjustable support member 170. The adjustable support member 110 will side within post 100 and adjustable support member 190 will slide within post 162 to control the desired position of the respective cheek pads of the face engagement elements 198 and 200. Preferably, the cheek pads should be centered on the noose of the weaver and the chin rest should be tucked snugly under the chin.

Next, knobs 90 and 152 are turned to adjust the position of the head of the wearer over the shoulders. By operating knobs 90 and 152, pressure is created against the chin by the chin rest 212 to lift the chin away from the chest of the wearer in a negative Z-axis direction. Likewise, the cheek pads of face engagement members 198 and 200, respectively, will use pressure to create a force to urge the head in a negative Z-axis direction. When used with the forces created by the of the face engagement elements 198 and 200 and the chin rest 212 will improve cervical lordosis and correct the malpositioned cranium that results from FHT or FHP. Lifting the chin and providing negative Z translation of the head, will move the location of the ears relative to the shoulders of the wearer thereby retracting the head to an anatomically desired position and thus improve the wearer's overall posture.

Preferably, the translation correction assembly 268 is used to create a fulcrum on which the head will pivot in order to correct the lordosis of the cervical spine. In use, after the collar 10 is mounted on the user, the position of the translation correction assembly 268 can be adjusted so that it will engage the neck of the user. A first adjustment is made along a line parallel to the Z-axis by turning the knob 288 clockwise. Turning the knob 288 clockwise will release the neck engagement member 278 from its nested position within the base 28. The neck engagement member 278 will progressively and incrementally move toward the neck of the user until it engages the neck, at either C1 to C7 of the cervical spine. The level in which the neck engagement member 278 will engage a given cervical spine (C1 through C7) can be adjusted further by pressing the plunger assembly 266 to release the locking mechanism 304 so that the correction assembly 268 can be adjusted toward or away from the shoulder of the wearer. The adjustment after pressing the plunger assembly 266 allows the position of the neck engagement member 278 to move toward the top of the base or toward the bottom of the base 242, the displacement being limited by the guides 306A and 306B. Once the desired anatomical position is achieved, the plunger assembly is released which in turn releases the compressed springs 280 and 282 which extend between the first plate 270 and second plate 272. The release of the plunger assembly 266 also permits the compressing spring 296 to extend and lock the locking mechanism 304 in place within one of the guides 306A, 306B and either 308 or 310. Then, the neck engagement member 278 can be extended further by turning the knob 288 to create a fulcrum and corrective force in the anterior direction along the Z-Axis.

The corrective force created by the neck engagement member 278 is preferably used with the engagement of the chin rest 212 and the cheek pads 198 and 200. The corrective force will cause the head to translate in a Y-axis and a negative Z-axis direction, by a pivoting action in which the head pivots about the fulcrum to correct the position of the head and to address the curvature of the cervical spine. The movement is advantageously used to correct the posture of the wearer by therapeutically addressing the negative effects of FHT and helping the wearer achieve better overall posture of his or her body.

The collar 10 has many benefits. Because the FHT or FHP is a position that produces damaging structural stress on the entire spine it is reasonable to apply the collar in post-operative spine surgery patients. This applies to cervical, thoracic, or lumbo-pelvic post-surgical procedures. This allows healing of the spinal joints without the damaging shear and moment mechanical stresses produced by the forward head posture position. For the above reasons the collar assembly 10 may also be used in post-traumatic situations from car accidents or sports injuries, etc. Therefore hospitals, emergency medical technicians, paramedics and other medical providers will desirably employ its use. The lordosis correction assembly can also be used with conventional cervical collars where forward head posture correction may be difficult, i.e., with older patients where fusion of spinal joints has advanced to a point where minimal movement is possible. These conditions will still benefit from some mild lordosis support. This will reduce some of the mechanical strain and pain in these patients.

Figure 21:
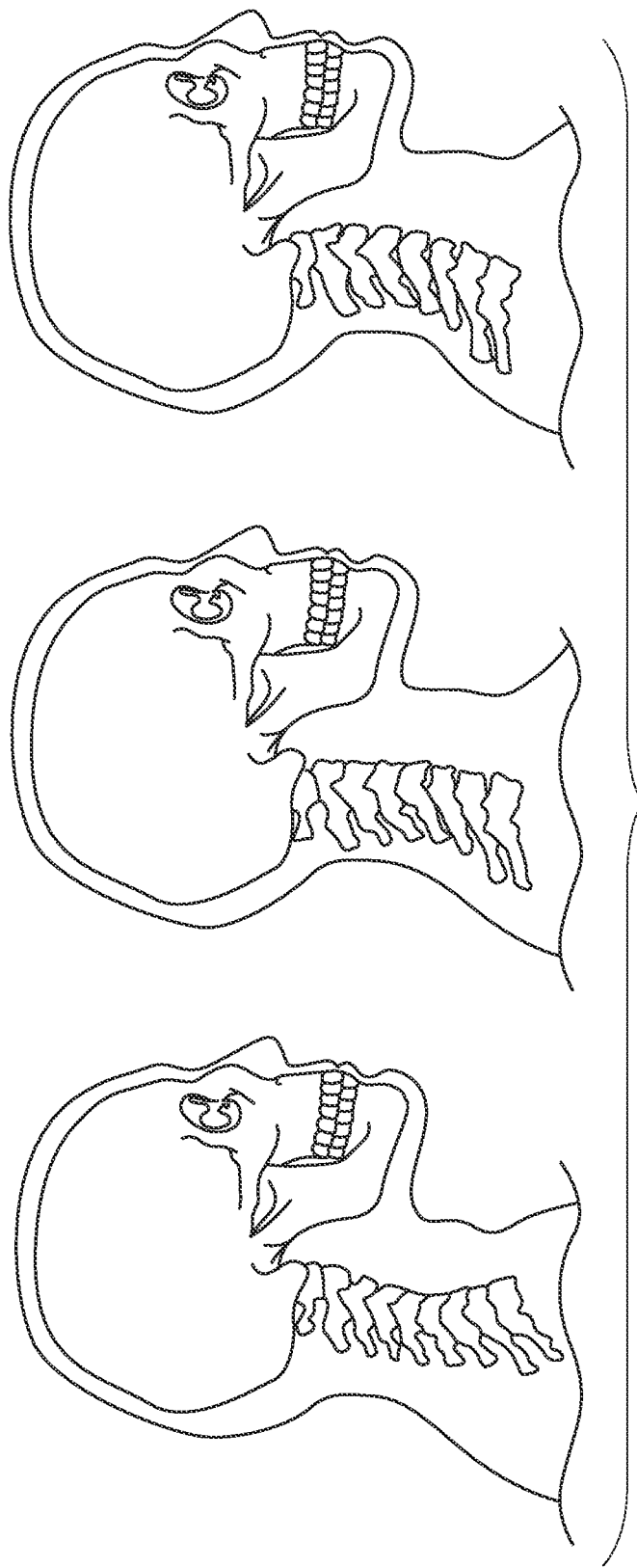
FIG. 21 is a schematic cross sectional view depicting sequential changes of the forward head translation and cervical spine configuration to correct head translation relative to the shoulders.
Figure 22:
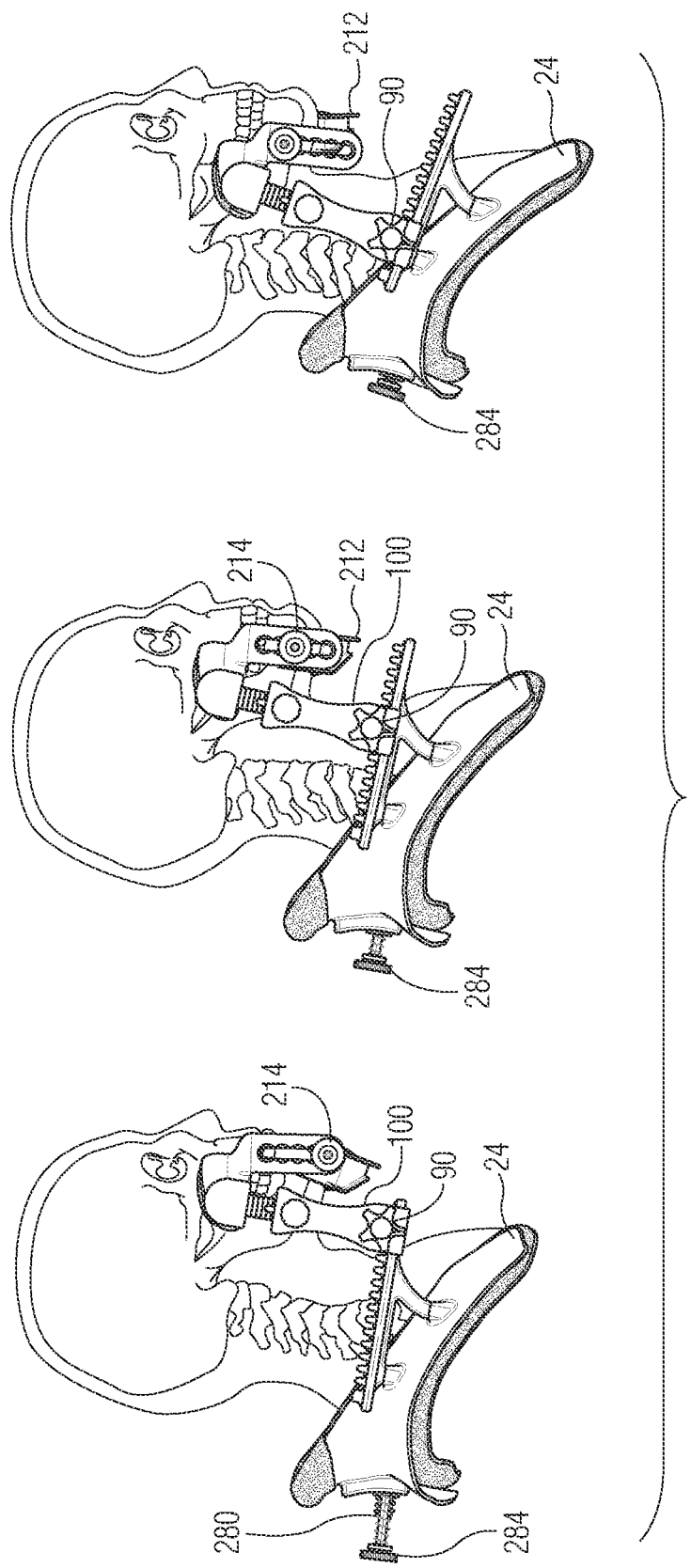
FIG. 22 is schematic side view depicting sequential changes that occurs in the wearer's head positon and spinal configuration as successive steps and time wise-incremental adjustment are carried out by means of the present invention.

The progressive improvement of the cervical lordosis requires precise support to the offending misaligned vertebrae. As shown in FIGS. 21 and 22, as treatment progresses from A to B in approximately one month, B shows the head moved in the negative Z direction to align over the shoulders. There is no extension or flexion movement required. A full contoured support would not be sufficient because it spreads the support over a large area, C1-C7. Finally, the neck curve has been restored to normal and the forward head posture has been repositioned over the shoulders by the collar's upward angled −Z directional movement, as illustrated in position C. These motions and intended clinical correction of forward head posture and cervical lordosis as well as kyphosis, which are not discussed in the prior art and could not be achieved by the prior art because there must be simultaneous correction of both forward head posture and a precise support to the misaligned cervical vertebrae in order to change the cervical kyphosis into a cervical lordosis. This treatment will prevent cervical arthritis and cervical disc degeneration and painful neck misalignments.

As such, from the foregoing detailed description, it will be evident that there are a number of changes, adaptations and modifications of the present invention which come within the others of those of ordinary skill in the art. Accordingly, the embodiments shown in the drawings are for purposes of illustrating the manner in which the present invention can be applied without, however, excluding other applications that fall within the spirit and scope of the appended claims. While the present invention has been set forth in terms of specific embodiments thereof, the instant disclosure is such that numerous variations upon the invention are now enabled to those skilled in the art, which variations yet reside within the scope of the present teachings. Therefore, the invention is to be broadly construed and limited only by the scope and spirit of the claims now appended hereto. The description of the material used applies to all embodiments described herein, it be understood that the invention covers equivalent material known in the medial and manufacturing arts, which are acceptable to governmental agencies, such as the United States Food and Drug Administration. The embodiments shown are exemplary and it is contemplated that other equivalent forms can be used within the scope of the objects of the invention.

The invention claimed is:

1. An adjustable collar, comprising:
   a support structure having a shoulder pad with at least one edge and a surface that are anatomically shaped and dimensioned to wrap around a portion of a body of a wearer, wherein said shoulder pads have free ends which define a pair of opposed arms that are joined at a proximal end to a rear base that is shaped and dimensioned to be curved relative to a shoulder and a neck area of the body of the wearer, the distance intermediate said free ends of said pair of opposed arms form an opening having a given size;
   an adjustable structure connected to said support structure for predetermined incremental movement thereto, said adjustable structure having a first rack and pinion mechanism on which is mounted a first adjustment structure and having a second rack and pinion mechanism on which is mounted a second adjustment structure, wherein said first rack and pinion mechanism includes a first rotatable knob that enables said first adjustment structure to move relative to a longitudinal axis of said support structure from a first condition to a second condition in stepwise incremental fashion and wherein said second rack and pinion mechanism has a second rotatable knob that enables said second adjustment structure to move relative to said longitudinal axis from a first condition to a second condition in step-wise incremental fashion;
   a first pad configured to engage a portion of a first zygomatic area of a head of the wearer, said first pad being pivotally attached to a first shaft that is adapted to be adjustably and telescopingly moved within said first adjustment structure to position said first pad to a predetermined desired position relative to the first zygomatic area;
   a second pad configured to engage a portion of a second zygomatic area of the head of the wearer opposite to said first pad, said second pad being pivotally attached to a second shaft that is adapted to be adjustably and telescopingly moved within said second adjustment structure to position said second pad to a predetermined desired position relative to the second zygomatic area;
   a support rest configured to engage a mandible area of the head of the wearer, said support rest having a first side slidably joined to said first pad and having a second side slidably joined to said second pad; and
   an adjustable displacement mechanism having a support base that is joined to the rear base of said support structure and a plunger assembly having a neck engagement member connected to a pair of spring loaded guide posts that are operatively joined to a rotatable knob that is adapted to displace said neck engagement member relative to a Z-axis of said support structure, whereby operating said rotatable knob will displace said neck engagement member in a direction along a line parallel to the Z-axis to apply pressure against the neck area of the body of the wearer to translate the head of the wearer to a predetermined desired condition.

2. The adjustable collar according to claim 1, wherein said first side of said support rest is rotatably secured to said first pad by a first guide member having a plurality of recesses to enable said first side of said support rest to be adjusted to a desired position and said second side of said support rest is rotatably secured to said second pad by a second guide member having a plurality of recesses to enable said second side of said support rest to be adjusted to a desired position, whereby said support rest is adapted to lift a mandibular portion of the head of the wearer away from a cheek area of the body of the wearer to assist in translating the head of the wearer along a Y-axis and the Z-axis.

3. The adjustable collar according to claim 2, wherein operating said first rack and pinion mechanism and said second rack and pinion mechanisms moves said first adjustment structure and second adjustment structure, respectively, to enable said first pad and said second pad to urge the head of the wearer in a negative Z-Axis direction.

4. The adjustment collar according to claim 3, wherein operating said first rack and pinon mechanism, operating said second rack and pinion mechanism and adjustments to said neck engagement member are therapeutically used to correct forward translation of the head of the wearer.

5. The adjustable collar according to claim 2 operating said first rack and pinion mechanism moves said first adjustment structure to enable said first pad to create a force to urge the head of the wearer in a negative Z-Axis direction.

6. The adjustable collar according to claim 1, wherein said first shaft is adapted to slide relative to said first adjustment structure to incrementally position said first pad to a desired position relative to the first zygomatic area, wherein said desired positioned of the first pad is secured by a first stopping mechanism.

7. The adjustable collar according to claim 6, wherein said second shaft is adapted to slide relative to said second adjustment structure to incrementally position said second pad to a desired position relative to the second zygomatic area, wherein said desired position of said second pad is secured by a second stopping mechanism.

8. The adjustable collar according to claim 1, wherein said free ends of said pair of opposed arms move toward and away from each other to expand and reduce said given size of said opening to enable said adjustable collar to be mounted on or removed from the body of the wearer.

9. The adjustable collar according to claim 1, wherein said support base has a slot so that the position of said neck engagement member is adjustable relative to a Y-axis of said support structure, to enable corrective forces to be applied to predetermined areas of a cervical spine area of the body of the wearer.

10. An adjustable collar comprising:
   a support structure having a member that is shaped and dimensioned to wrap around and configured to engage at least a portion of an upper area of a body of a wearer;
   an adjustable structure connected to said support structure adapted thereto for predetermined step-wise and progressive incremental movement along a line parallel to a longitudinal Z-axis of said support structure, said adjustable support structure having a first adjustable mechanism configured to engage a portion of a head of the wearer and a second adjustable mechanism configured to engage another portion of said head of the wearer;
   whereby a positon of the adjustable structure is adjustable relative to said support structure to cause the head of the wearer to translate to an anatomically desired position to correct forward head translation;
   a chin rest having a first and second side wherein the first side of said chin rest is adjustably and pivotally joined to said first adjustable mechanism and the second side of said chin rest is adjustably and pivotally joined to said second adjustable mechanism; and
   a translation correction assembly having a rotatable adjustment knob that is operatively secured to a spring loaded neck engagement member to engage and displace a portion of a neck of the wearer in a negative Z-axis direction to correct forward head translation;
   wherein the translation correction assembly includes a pair of guide posts having proximal ends attached to said spring loaded neck engagement member and distal ends joined to a plate that limits movement of said rotatable adjustment knob toward and away from said support structure, which enables said spring loaded neck engagement member to apply incremental corrective forces against the neck to translate the head in a Y-axis and negative Z-axis direction thereby returning a curvature of a cervical spine to a therapeutically desired condition.

\* \* \* \* \*